United States Patent
Zhang et al.

(10) Patent No.: US 8,389,751 B2
(45) Date of Patent: Mar. 5, 2013

(54) SIMPLIFIED METHOD FOR PRODUCING ALKYLENE OXIDES WITH A HIGH EFFICIENCY CATALYST AS IT AGES

(75) Inventors: Liping Zhang, Lake Jackson, TX (US); William H. Henstock, Charleston, WV (US); Hwaili Soo, Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 376 days.

(21) Appl. No.: 12/763,276

(22) Filed: Apr. 20, 2010

(65) Prior Publication Data

US 2010/0267974 A1 Oct. 21, 2010

Related U.S. Application Data

(60) Provisional application No. 61/171,248, filed on Apr. 21, 2009.

(51) Int. Cl.
C07D 301/10 (2006.01)

(52) U.S. Cl. ...................................... 549/534

(58) Field of Classification Search .................... 549/534
See application file for complete search history.

(56) References Cited

U.S. PATENT DOCUMENTS

| | | | |
|---|---|---|---|
| 4,759,313 A | 7/1988 | Dye | |
| 4,761,394 A | 8/1988 | Lauritzen | |
| 4,766,105 A | 8/1988 | Lauritzen | |
| 4,769,047 A | 9/1988 | Dye | |
| 4,808,738 A | 2/1989 | Lauritzen | |
| 4,820,675 A | 4/1989 | Lauritzen | |
| 4,829,044 A | 5/1989 | Boxhoorn | |
| 4,831,162 A | 5/1989 | Nakajima | |
| 4,874,739 A | 10/1989 | Boxhoorn | |
| 4,874,879 A | 10/1989 | Lauritzen | |
| 4,908,343 A | 3/1990 | Bhasin | |
| 5,102,848 A | 4/1992 | Soo et al. | |
| 5,143,877 A | 9/1992 | Geus | |
| 5,145,824 A | 9/1992 | Buffum | |
| 5,155,242 A | 10/1992 | Shankar | |
| 5,228,484 A | 7/1993 | Johnson | |
| 5,262,551 A | 11/1993 | Horrell et al. | |
| 5,364,826 A | 11/1994 | Kemp | |
| 5,380,697 A | 1/1995 | Matusz | |
| 5,380,885 A | 1/1995 | Kemp | |
| 5,387,751 A | 2/1995 | Hayden et al. | |
| 5,418,202 A | 5/1995 | Evans | |
| 5,447,897 A | 9/1995 | Kemp | |
| 5,486,628 A | 1/1996 | Kemp | |

(Continued)

FOREIGN PATENT DOCUMENTS

| | | |
|---|---|---|
| CA | 1286687 | 7/1991 |
| EP | 0357292 A1 | 3/1990 |

(Continued)

OTHER PUBLICATIONS

International Search Report for PCT/US2010/031533 Written Opinion of The International Searching Authority for PCT/US2010/031533.

(Continued)

Primary Examiner — Taylor Victor Oh
(74) Attorney, Agent, or Firm — Hansen IP Law PLLC

(57) ABSTRACT

A simplified method of operating an alkylene oxide production process that utilizes a high efficiency silver catalyst is shown and described. The method accounts for declining catalyst activity that occurs as the catalyst ages by making alternating changes to the reaction temperature and an overall chloriding effectiveness parameter.

20 Claims, 6 Drawing Sheets

U.S. PATENT DOCUMENTS

| | | | |
|---|---|---|---|
| 5,504,053 | A | 4/1996 | Chou et al. |
| 5,519,152 | A | 5/1996 | Gorcester |
| 5,545,603 | A | 8/1996 | Kemp |
| 5,597,773 | A | 1/1997 | Evans |
| 5,663,385 | A | 9/1997 | Kemp |
| 5,703,253 | A | 12/1997 | Evans |
| 5,719,299 | A | 2/1998 | Raa |
| 5,739,075 | A | 4/1998 | Matusz |
| 5,770,746 | A | 6/1998 | Cooker |
| 5,801,259 | A | 9/1998 | Kowaleski |
| 5,840,932 | A | 11/1998 | Evans |
| 5,874,653 | A | 2/1999 | Van Kruchten |
| 5,929,259 | A | 7/1999 | Lockemeyer |
| 6,511,938 | B1 | 1/2003 | Liu |
| 7,615,655 | B2 * | 11/2009 | Zhang et al. .......... 549/534 |
| 2004/0198993 | A1 | 10/2004 | Matusz |

FOREIGN PATENT DOCUMENTS

| | | | |
|---|---|---|---|
| EP | 266015 | B1 | 12/1991 |
| EP | 0480537 | A1 | 4/1992 |
| EP | 352850 | | 1/1994 |
| EP | 480538 | B1 | 9/1998 |
| EP | 1458698 | B1 | 4/2005 |
| EP | 1458699 | | 11/2005 |
| EP | 1458699 | B1 | 11/2005 |
| GB | 1314613 | | 4/1973 |
| WO | 9713579 | A1 | 4/1997 |
| WO | 2005035513 | | 4/2005 |

OTHER PUBLICATIONS

International Search Report for PCT/US2010/031668 Written Opinion of The International Searching Authority for PCT/US2010/031668.

Notice of Opposition to European Patent No. 1,458,699 B1, filed with the European Patent Office (EPO) by The Dow Chemical Company, P.O. Box 1967, Midland, MI 4841-1967 (Aug. 3, 2006).

Notice of Opposition to European Patent No. 1,458,698 B1, filed with the European Patent Office (EPO) by The Dow Chemical Company, P.O. Box 1967, Midland, MI 4841-1967 (Jan. 18, 2006).

Reply in Opposition to European Patent No. 1,458,608 B1, filed with the European Patent Office (EPO) by The Dow Chemical Company, P.O. Box 1967, Midland, MI 4841-1967 (Aug. 22, 2008).

Berty, Chapter 8, Applied Industrial Catalysts, vol. 1 pp. 207-239 (1983).

* cited by examiner

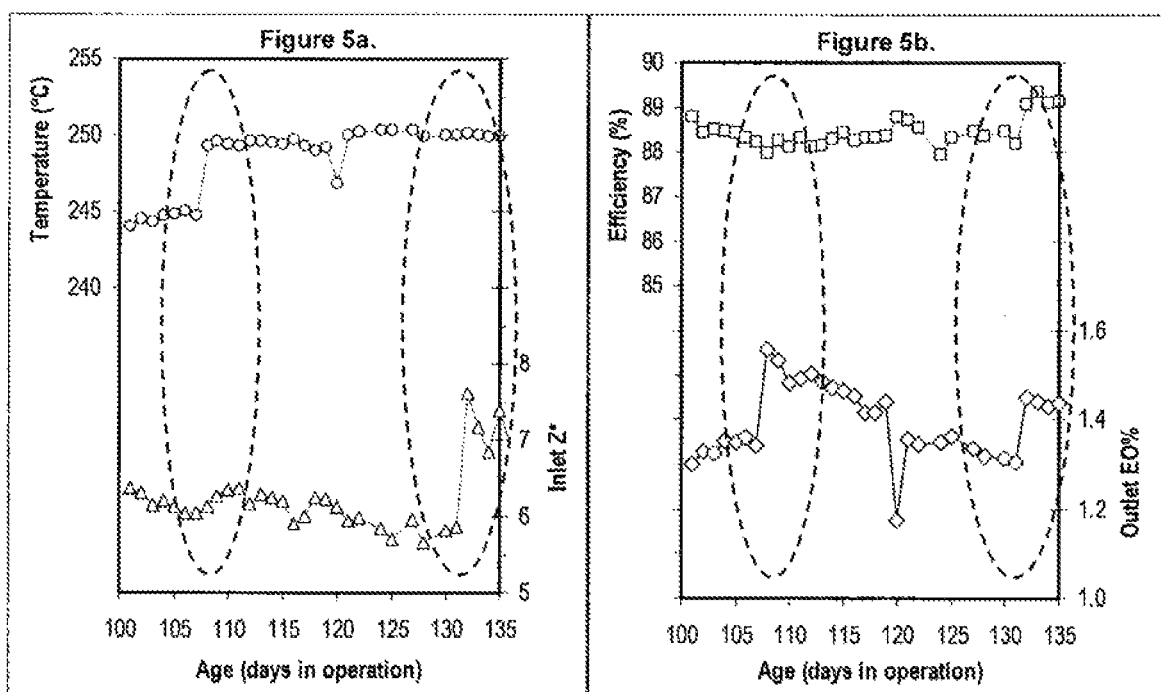

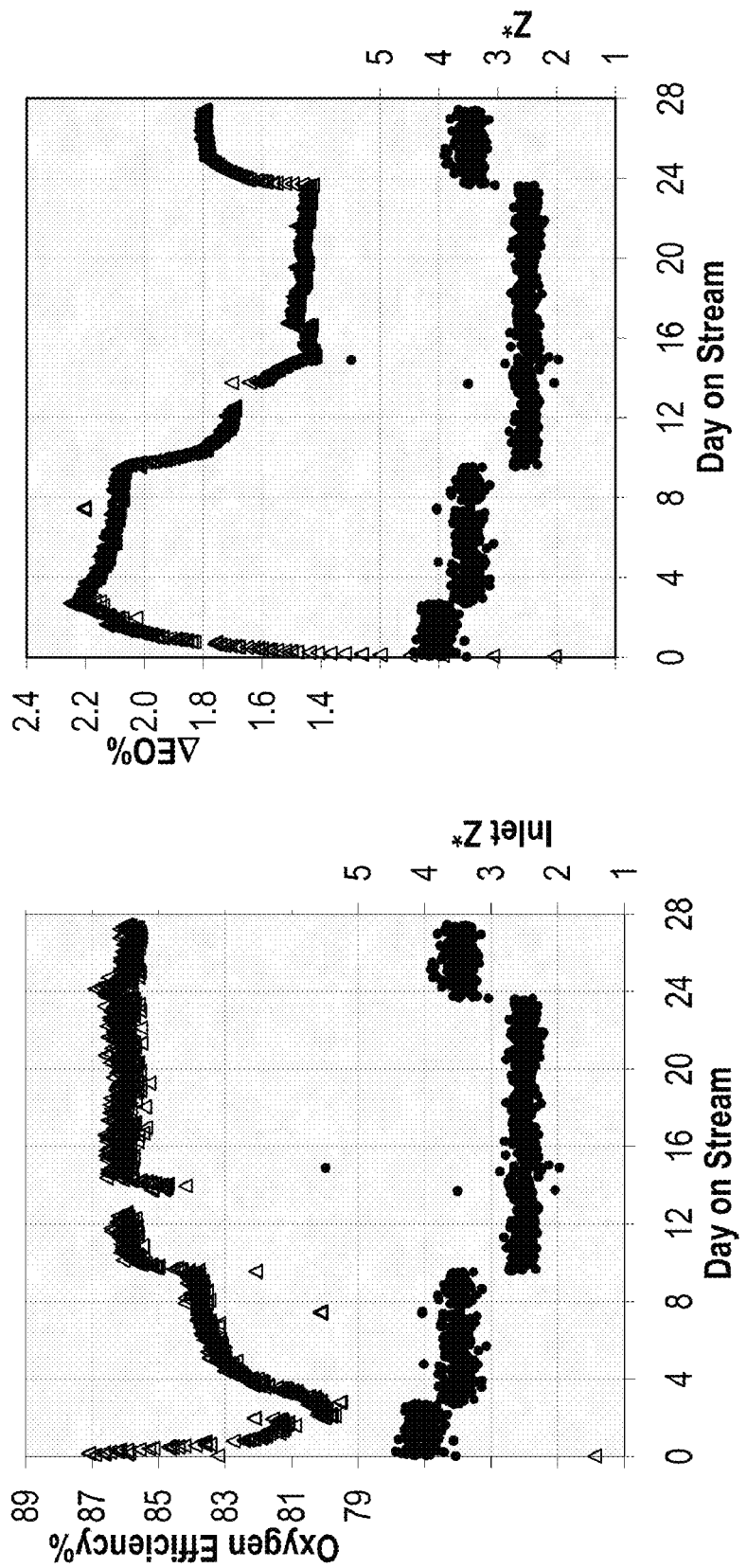

SIMPLIFIED METHOD FOR PRODUCING ALKYLENE OXIDES WITH A HIGH EFFICIENCY CATALYST AS IT AGES

CROSS-REFERENCE TO RELATED APPLICATIONS

This application claims the benefit of U.S. Provisional Application 61/171,248, filed on Apr. 21, 2009, the entirety of which is hereby incorporated by reference.

TECHNICAL FIELD

This disclosure relates generally to processes for making alkylene oxides, and more specifically, to a simplified method of operating alkylene oxide production processes using high efficiency catalysts as the catalyst ages.

BACKGROUND

Alkylene oxides are known for a multiplicity of utilities. Ethylene oxide, for example, is used to produce ethylene glycol, nonionic surfactants, glycol ethers, ethanolamines, and polyethylene polyether polyols. Ethylene glycol is used as an automotive coolant, as antifreeze, and in preparing polyester fibers and resins. Propylene oxide is used to produce propylene glycol and polypropylene polyether polyols, which are used in polyurethane polymer applications.

The production of alkylene oxides via catalytic epoxidation of olefins in the presence of oxygen using silver based catalysts is known. Conventional silver-based catalysts used in such processes typically provide a relatively lower efficiency or "selectivity" (i.e., a lower percentage of the reacted alkylene is converted to the desired alkylene oxide). In certain exemplary processes, when using conventional catalysts in the epoxidation of ethylene, the theoretically maximal efficiency towards ethylene oxide, expressed as a fraction of the ethylene converted, does not reach values above the 6/7 or 85.7 percent limit. Therefore, this limit had long been considered to be the theoretically maximal efficiency of this reaction, based on the stoichiometry of the following reaction equation:

$$7C_2H_4 + 6O_2 \rightarrow 6C_2H_4O + 2CO_2 + 2H_2O$$

cf. Kirk-Othmer's Encyclopedia of Chemical Technology, 4th ed., Vol. No. 9, 1994, p. 926.

Certain "high efficiency" or "high selectivity" modern silver-based catalysts are highly selective towards alkylene oxide production. For example, when using certain modern catalysts in the epoxidation of ethylene, the theoretically maximal efficiency towards ethylene oxide can reach values above the 6/7 or 85.7 percent limit referred to, for example 88 percent, or 89 percent, or above. As used herein, the terms "high efficiency catalyst" and "high selectivity catalyst" refer to a catalyst that is capable of producing an alkylene oxide from the corresponding alkylene and oxygen at an efficiency greater than 85.7 percent. The observed actual efficiency of a high efficiency catalyst may fall below 85.7 percent under certain conditions based on process variables, catalyst age, etc. However, if the catalyst is capable of achieving at least an 85.7 percent efficiency, at any point during its life, for example, under any set of reaction conditions as described in the Examples hereinafter, or by extrapolating lower efficiencies observed at two different oxygen conversions obtained by varying gas hourly space velocity to the limiting case of zero oxygen conversion, it is considered to be a high efficiency catalyst. Such highly efficient catalysts, which may comprise as their active components silver, rhenium, at least one further metal, and optionally, a rhenium co-promoter, are disclosed in EP0352850B1 and in several subsequent patent publications. "Promoters," sometimes referred to as "inhibitors" or "moderators," refer to materials that enhance the performance of the catalysts by either increasing the rate towards the desired formation of alkylene oxide and/or suppressing the undesirable oxidation of olefin or alkylene oxide to carbon dioxide and water, relative to the desired formation of alkylene oxide. As used herein, the term "co-promoter" refers to a material that—when combined with a promoter—increases the promoting effect of the promoter. In addition, promoters may also be referred to as "dopants." In the case of those promoters that provide high efficiencies, the terms "high efficiency dopants" or "high selectivity dopants" may be used.

"Promoters" can be materials that are introduced to catalysts during the preparation of the catalysts (solid phase promoters). In addition, "promoters" can also be gaseous materials that are introduced to the epoxidation reactor feed (gas phase promoters). In one example, an organic halide gas phase promoter may be added continuously to the epoxidation reactor feed to increase the catalyst efficiency. For silver-based ethylene epoxidation catalysts, both solid and gas phase promoters are typically required in any commercial processes.

All silver based catalysts used in alkylene oxide production processes are subject to an aging-related performance decline during normal operation, and they need to be exchanged periodically. The aging manifests itself by a reduction in the activity of the catalyst and may also manifest itself by a reduction in efficiency. Usually, when a reduction in catalyst activity occurs, the reaction temperature is increased in order to maintain a constant alkylene oxide production rate. The reaction temperature may be increased until it reaches the design limit or becomes undesirably high, or the efficiency may become undesirably low, at which point in time the catalyst is deemed to be at the end of its lifetime and would need to be exchanged or regenerated. Current industry practice is to discharge and replace the catalyst when it is at the end of its useful life. The silver is recovered and promoters may be recovered from the discharged catalyst.

Conventional catalysts have relatively flat efficiency curves with respect to the gas phase promoter concentration in the feed, i.e., the efficiency is almost invariant (i.e., the change in efficiency with respect to a change in gas phase promoter concentration in the feed is less than about 0.1%/ppmv) over a wide range of promoter concentrations, and this invariance is substantially unaltered as reaction temperature is changed during prolonged operation of the catalyst. However, conventional catalysts have nearly linear activity decline curves with respect to the gas phase promoter concentration in the feed, i.e., with increasing gas phase promoter concentration in the feed, temperature has to be increased or the alkylene oxide production rate will be reduced. Therefore, when using a conventional catalyst, for optimum efficiency, the gas phase promoter concentration in the feed can be chosen at a level at which the maximum efficiency can be maintained at relatively lower operating temperatures. Typically, the gas phase promoter concentration can remain substantially the same during the entire lifetime of a conventional catalyst. On the other hand, the reaction temperature may be adjusted to obtain a desired production rate without any substantial impact on efficiency due to non-optimal gas phase promoter concentration.

By contrast, high efficiency catalysts tend to exhibit relatively steep efficiency curves as a function of gas phase promoter concentration as the concentration moves away from the value that provides the highest efficiency (i.e., the change in efficiency with respect to a change in gas phase promoter concentration is at least about 0.2%/ppmv when operating away from the efficiency maximizing promoter concentration). Thus, small changes in the promoter concentration can result in significant efficiency changes, and the efficiency exhibits a pronounced maximum, i.e. an optimum, at certain concentrations (or feed rates) of the gas phase promoter, when reactor pressure and feed gas composition are kept unchanged for a given reaction temperature and catalyst age. Moreover, the efficiency curves and the optimum gas phase promoter concentration tend to be strong functions of reaction temperature and are thus significantly affected if reaction temperature is varied, for example, to compensate for decreases in catalyst activity (i.e., the change in efficiency with respect to a change in reaction temperature can be at least about 0.1%/° C. when operating away from the efficiency maximizing promoter concentrations for the selected temperatures). In addition, rhenium-promoted high efficiency catalysts have exhibited significant activity increases with increases in the gas phase promoter concentration in the feed, i.e., with increasing gas phase promoter concentration in the feed, temperature has to be decreased or the production rate will increase. Thus, for conventional catalysts, the rate of alkylene oxide production is typically controlled by adjusting reaction temperature, while for high efficiency catalysts gas phase promoter concentration and/or reaction temperature may be adjusted to control the rate.

To address the strong influence of reaction temperature and gas phase promoter concentration on the efficiency of high efficiency catalysts, it has been proposed to use the temperature differential to first calculate the new gas phase promoter concentration. The gas phase promoter concentration changes are made whenever the reaction temperature is changed (U.S. Pat. No. 7,193,094; European Patent No. 1,458,699). However, this technique increases the complexity of the process and the controls that are required for automated operation. It can also result in excessive or insufficient gas phase promoter consumption and increase the sensitivity of the process to disturbances in reaction temperature. It also requires knowledge of a mathematical relationship between temperature and efficiency, which may be difficult or costly to obtain. Finally, this method only takes into account the variation in optimum promoter concentration with temperature and does not take into account the fact that the optimum promoter concentration can also be a function of other process variables such as catalyst age. Thus, a need has arisen for a process that addresses the foregoing issues.

SUMMARY

In accordance with one aspect, a process for manufacturing an alkylene oxide by reacting a feed gas comprising an alkylene, oxygen, and at least one organic chloride over a high efficiency silver catalyst to yield a reaction product comprising the alkylene oxide is provided. The feed gas has an overall catalyst chloriding effectiveness, and the reaction is carried out at a reaction temperature. The process comprises varying the overall catalyst chloriding effectiveness of the feed gas and the reaction temperature in an alternating sequence such that when one of the overall catalyst chloriding effectiveness and the reaction temperature is varied, the other of the overall catalyst chloriding effectiveness and the reaction temperature is maintained at a substantially constant value for a selected period of time. In certain illustrative embodiments, the step of varying the overall catalyst chloriding effectiveness and the reaction temperature in an alternating sequence comprises varying an alternating one of the overall catalyst chloriding effectiveness and the reaction temperature in response to a selected decrease in the concentration of the alkylene oxide in the reaction product or a selected decrease in the yield of the alkylene oxide.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

FIG. 5A is a graph depicting a relationship between reaction temperature, an overall chloriding effectiveness parameter, and catalyst age for a process of making ethylene oxide by epoxidizing ethylene;

FIG. 5B is a graph depicting a relationship between catalyst efficiency and reactor effluent ethylene oxide concentration and catalyst age for a process of making ethylene oxide by epoxidizing ethylene;

FIG. 6A is a graph depicting a relationship between catalyst efficiency, an overall catalyst chloriding parameter, and catalyst age for a process of making ethylene oxide by epoxidizing ethylene; and FIG. 6B is a graph depicting a relationship between reactor effluent ethylene oxide concentration, an overall chloriding effectiveness parameter, and catalyst age for a process of making ethylene oxide by epoxidizing ethylene.

DETAILED DESCRIPTION

Figure 1:
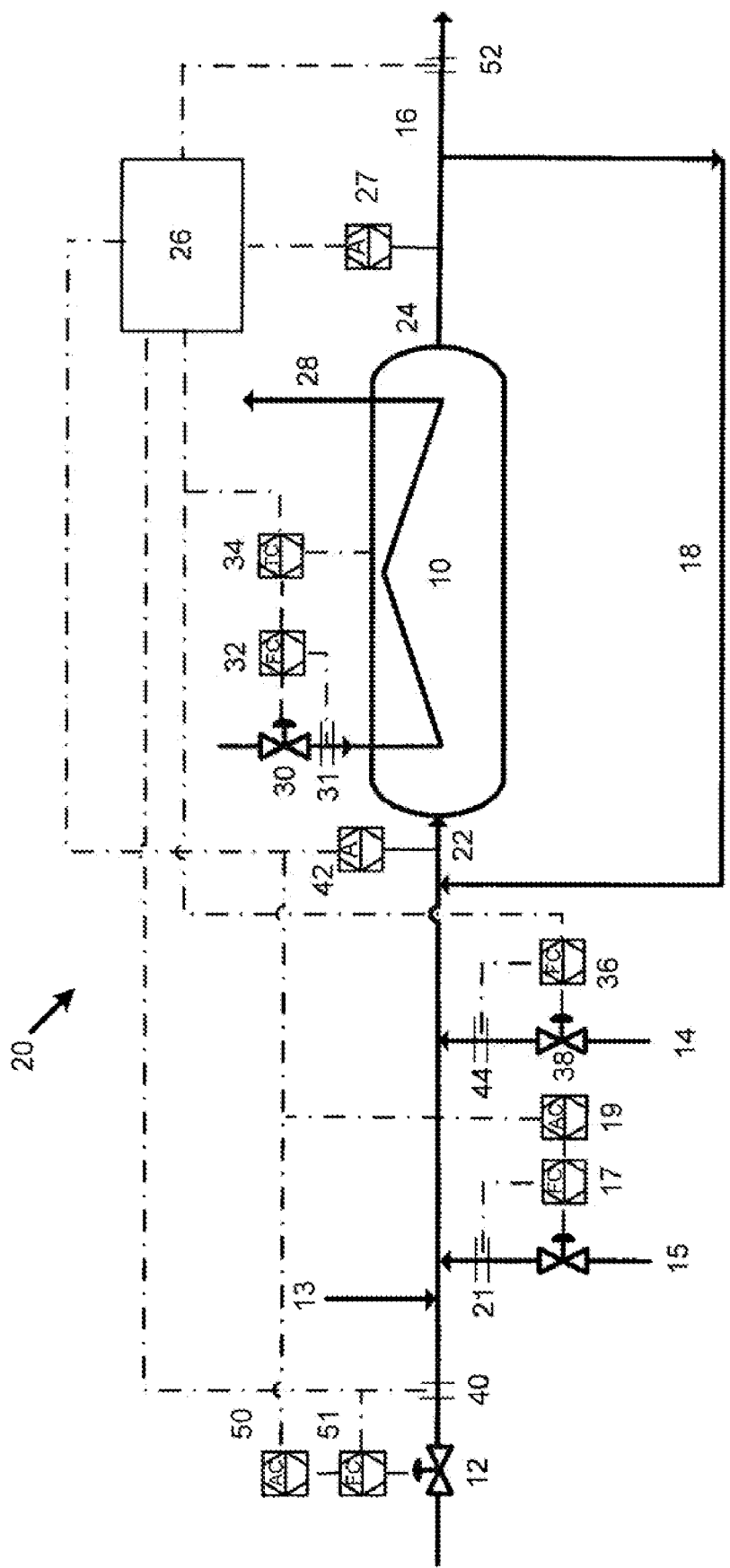
FIG. 1 is a process flow diagram depicting an embodiment of a process for making an alkylene oxide by epoxidizing an olefin.

As discussed below, the present disclosure provides a simplified method of operating a process for making an alkylene oxide using a high efficiency catalyst as the catalyst ages. The process comprises varying the overall chloriding effectiveness and the reaction temperature in an alternating sequence to compensate for reductions in catalyst activity due to aging.

In order to facilitate an understanding of the present disclosure, it is useful to define certain terms relating to catalyst and process performance. The "activity" of a catalyst in a fixed bed reactor is generally defined as the reaction rate towards the desired product per unit of catalyst volume in the reactor. The activity relates to both the total number of available active sites and the reaction rate of each site. The number of active sites can be reduced in several ways. For example, they can be reduced by coalescence of the silver particles, which reduces the surface area of the silver available for reaction. They can also be reduced by poisoning, for example by reaction with trace sulfur compounds in the reactor feed. The number of active sites can also be reduced by reaction with normal process constituents, such as by reaction with chloride compounds in the process stream to form silver chloride compounds, which are inactive towards the epoxidation reaction. The activity will also decline if the reaction rate goes down for at least some of the active sites (e.g., due to localized poisoning) independent of the total number of active sites. To compensate for the activity decline in order to maintain a given production rate, certain reaction conditions have to be changed to increase the overall production rate of the available active sites. For instance, reaction temperature is often raised to provide more energy to the active sites for this purpose. "Activity" can be quantified in a number of ways, one being the mole percent of alkylene oxide contained in the outlet stream of the reactor relative to that in the inlet stream (the mole percent of alkylene oxide in the inlet stream typically, but not necessarily, approaches zero percent) while the reaction temperature is maintained substantially constant; and another being the temperature required to maintain a given rate of alkylene oxide production. In many instances, activity is measured over a period of time in terms of the mole percent of alkylene oxide produced at a specified constant temperature. Alternatively, activity may be measured as a function of the temperature required to sustain production of a specified constant mole percent of alkylene oxide, such as ethylene oxide, given other conditions such as pressure and total moles in the feed.

The "efficiency" of the epoxidation, which is synonymous with "selectivity," refers to the relative amount (as a fraction or in percent) of converted or reacted olefin that forms a particular product. For example, the "efficiency to alkylene oxide" refers to the percentage on a molar basis of converted or reacted olefin that forms alkylene oxide. One measure of the useful life of a catalyst is the length of time that reactants can be passed through the reaction system during which time acceptable productivity is obtained in light of all relevant factors. The "yield" of alkylene oxide refers to the net number of moles of alkylene oxide produced by the process divided by the net number of moles of olefin fed to the process for any given time period.

FIG. 1 illustrates a process 20 for making an alkylene oxide. Process 20 includes a reactor 10 comprising a tubular vessel with a catalyst bed disposed in it. Although depicted in a horizontal orientation in FIG. 1, commercial embodiments of reactor 10 are typically vertically oriented. Olefin (i.e., alkylene) feed stream 12 (which may also include saturated hydrocarbons, such as ethane, as an impurity) is combined with oxygen feed 15 and gas phase promoter feed 14 to define reactor feed stream 22 proximate the reactor inlet. Reactor product stream 24 includes the alkylene oxide ("AO") product, plus side products (e.g., $CO_2$, $H_2O$, and small amounts of saturated hydrocarbons), unreacted olefin, oxygen, and inerts. In commercial processes, the alkylene oxide product along with some water product is removed from the reactor product stream 24 in an alkylene oxide recovery unit (not shown). If desired, recycle stream 18 may also be provided to recycle the unreacted olefins and oxygen, in which case net product stream 16 is also provided. However, if a recycle stream 18 is provided, a purge line is preferably provided to reduce the build up of impurities and/or side products such as argon and ethane. In addition, commercial processes also include a carbon dioxide removal step that is performed upstream of where recycle stream 18 combines with the fresh feed and enters the reactor 10.

The olefin comprising olefin feed stream 12 may be any olefin, including aromatic olefins and di-olefins, whether conjugated or not. However, preferred olefins are mono-olefins having the following formula:

wherein, $R_1$ and $R_2$ are individually selected from the group consisting of hydrogen and alkyl radicals having from 1 to 6 carbon atoms. Propylene ($R_1$=$CH_3$, $R_2$=H) and ethylene ($R_1$=$R_2$=H) are more preferred, and ethylene is most preferred. Correspondingly, preferred alkylene oxides in reactor product stream 24 are of the formula:

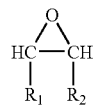

wherein, $R_1$ and $R_2$ are individually selected from the group consisting of hydrogen and alkyl radicals having from 1 to 6 carbon atoms. Propylene oxide ($R_1$=$CH_3$, $R_2$=H) and ethylene oxide ($R_1$=$R_2$=H) are most preferred, and ethylene oxide is especially preferred.

Oxygen feed 15 may comprise substantially pure oxygen or air. If pure oxygen is used, ballast gases or diluents 13 such as nitrogen or methane may also be included to maintain the oxygen concentration below the maximum level allowed by flammability considerations. The concentration of oxygen in reactor feed stream 22 may vary over a wide range, and in practice, flammability is generally the limiting factor for oxygen concentration. Generally, the oxygen concentration in reactor feed 22 will be at least about one (1) mole percent and preferably at least about two (2) mole percent. The oxygen concentration will generally be no more than about fifteen (15) mole percent and preferably no more than about twelve (12) mole percent. The ballast gas 13 (e.g., nitrogen or methane) is generally from about 50 mole percent to about 80 mole percent of the total composition of reactor feed stream 22. One reason methane ballast gas is preferred over nitrogen is because, due to its higher heat capacity, methane facilitates the use of higher oxygen concentrations in the cycle, and therefore, improves both activity and efficiency.

The concentration of olefin in reactor feed stream 22 may vary over a wide range. However, it is preferably at least about eighteen (18) mole percent and more preferably at least about twenty (20) mole percent. The concentration of olefin in reactor feed stream 22 is preferably no greater than about 50 mole percent, and more preferably is no greater than about 40 mole percent.

When present, the carbon dioxide concentration in reactor feed stream 22 has a large adverse effect on the efficiency, activity and/or stability of catalysts used in reactor 10. Carbon dioxide is produced as a reaction by-product and may also be introduced with other inlet reaction gases as an impurity. In commercial ethylene epoxidation processes, at least part of the carbon dioxide is removed continuously in order to control its concentration to an acceptable level in the cycle. The carbon dioxide concentration in reactor feed 22 is generally no more than about 5 mole percent, preferably no more than about 3 mole percent, and even more preferably no more than about 2 mole percent of the total composition of reactor feed 22. Water may also be present in the feed gases in concentrations that are preferably from 0 to no more than about two (2) mole percent.

The gas phase promoter is generally a compound that enhances the efficiency and/or activity of process 20 for producing the desired alkylene oxide. Preferred gas phase promoters include organic chlorides. More preferably, the gas phase promoter is at least one selected from the group consisting of methyl chloride, ethyl chloride, ethylene dichloride, vinyl chloride, and mixtures thereof. Ethyl chloride and ethylene dichloride are most preferred as the gas phase promoter feed (stream 14). Using chlorohydrocarbon gas phase promoters as an example, it is believed that the ability of the promoter to enhance the performance (e.g., efficiency and/or activity) of process 20 for the desired alkylene oxide depends on the extent to which the gas phase promoter chlorinates the surface of the catalyst in reactor 10, for example, by depositing particular chlorine species such as atomic chlorine or chloride ions on the catalyst. However, hydrocarbons lacking chlorine atoms are believed to strip chlorides from the catalyst, and therefore, detract from the overall performance enhancement provided by the gas phase promoter. Discussions of this phenomenon may be found in Berty, "Inhibitor Action of Chlorinated Hydrocarbons in the Oxidation of Ethylene to Ethylene Oxide," *Chemical Engineering Communications*, Vol. 82 (1989) at 229-232 and Berty, "Ethylene Oxide Synthesis," *Applied Industrial Catalysis*, Vol. I (1983) at 207-238. Paraffinic compounds, such as ethane or propane, are believed to be especially effective at stripping chlorides from the catalyst. However, olefins, such as ethylene and propylene, are also believed to act to strip chlorides from the catalyst. Some of these hydrocarbons may also be introduced as impurities in the ethylene feed 12 or may be present for other reasons (such as the use of recycle stream 18). Typically, the preferred concentration of ethane in the reactor feed 22, when present, is from 0 to about 2 mole percent. Given the competing effects of the gas phase promoter and the chloride-removing hydrocarbons in reactor feed stream 22, it is convenient to define an "overall catalyst chloriding effectiveness value" that represents the net effect of the promoting and non-promoting gas phase species in halogenating (or chloriding) the catalyst. In the case of organic chloride gas-phase promoters, the overall catalyst chloriding effectiveness can be defined as the dimensionless quantity $Z^*$ and represented by the following formula:

$$Z^* = \frac{\text{ethyl chloride equivalent }(ppmv)}{\text{ethane equivalent (mole percent)}} \quad (1)$$

wherein the ethyl chloride equivalent is the concentration in ppmv (which is equivalent to ppm mole) of ethyl chloride that provides substantially the same catalyst chloriding effectiveness of the organic chlorides present in reactor feed stream 22 at the concentrations of the organic chlorides in feed stream 22; and the ethane equivalent is the concentration of ethane in mole percent that provides substantially the same catalyst dechloriding effectiveness of the non-chloride containing hydrocarbons in the reactor feed stream 22 at the concentrations of the non-chloride containing hydrocarbons in the reactor feed stream 22.

If ethyl chloride is the only gaseous chloride-containing promoter present in reactor feed stream 22, the ethyl chloride equivalent (i.e., the numerator in equation (1)) is the ethyl chloride concentration in ppmv. If other chlorine-containing promoters (specifically vinyl chloride, methyl chloride or ethylene dichloride) are used alone or in conjunction with ethyl chloride, the ethyl chloride equivalent is the sum of the concentration of ethyl chloride in ppmv plus the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed of 1 ppmv ethylene dichloride and 1 ppmv ethyl chloride, the ethyl chloride equivalent in the numerator of $Z^*$ would then be 3 ppmv. As a further example, it has been found that for certain catalysts methyl chloride has about 10 times less the chloriding effectiveness of ethyl chloride. Therefore, for such catalysts the ethyl chloride equivalent for a given concentration of methyl chloride in ppmv is 0.1× (methyl chloride concentration in ppmv). It has also been found that for certain catalysts, vinyl chloride has the same chloriding effectiveness as ethyl chloride. Therefore, for such catalysts the ethyl chloride equivalent for a given concentration of vinyl chloride in ppm is 1.0× (vinyl chloride concentration in ppmv). When more than two chlorine-containing promoters are present in reactor feed stream 22, which is often the case in commercial ethylene epoxidation processes, the overall ethyl chloride equivalent is the sum of the corresponding ethyl chloride equivalents for each individual chlorine-containing promoter that is present. As an example, for a hypothetical feed of 1 ppmv ethylene dichloride, 1 ppmv ethyl chloride, and 1 ppmv vinyl chloride, the ethyl chloride equivalent in the numerator of $Z^*$ would be 2*1+1+1*1=4 ppmv.

The ethane equivalent (i.e., the denominator in equation (1)) is the concentration of ethane in mole percent in reactor feed stream 22 plus the concentrations of the other hydrocarbons effective in removing chloride from the catalysts, corrected for their effectiveness for dechlorination relative to ethane. The relative effectiveness of ethylene compared to ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane. As a way of further illustration, if with a feed composition comprising an ethylene concentration of 30.0 mole percent and an ethane concentration of 0.30 mole percent, a level of 6.0 ppmv ethyl chloride equivalents is found to provide the same level of catalyst performance as 3.0 ppmv ethyl chloride equivalents with a similar feed composition but lacking ethane, then the ethane equivalent for 30.0 mole percent ethylene would be 0.30 mole percent. For a typical inlet reactor feed 22 having 30.0 mole percent ethylene and 0.1 mole percent ethane, the ethane equivalent then will be 0.4 mole percent. For an inlet reactor feed 22 having 30.0 mole percent ethylene and 0.3 mole percent ethane, the ethane equivalent will then be 0.6 mole percent. As another illustration, it has been found that for certain catalysts methane has about 500 times less the dechloriding effectiveness of ethane. Thus, for such catalysts the ethane equivalent for methane is 0.002× (methane concentration in mol %). For an inlet reactor feed 22 having 30.0 mole percent ethylene, 50 mole percent methane, and 0.1 mole percent ethane, the ethane equivalent will be 0.5 mole percent. The relative effectiveness of hydrocarbons other than ethane and ethylene can be measured experimentally by determining the inlet ethyl chloride equivalent concentrations required to achieve the same catalyst performance for a feed comprising the hydrocarbon of interest at its concentration in the feed at two different concentrations of ethane in the feed. If a hydrocarbon compound is found to have a very small dechloriding effect and is also present in low concentrations, then its contribution to the ethane equivalent concentration in the Z* calculation may be negligible.

Thus, given the foregoing relationships, in the case where reactor feed stream 22 includes ethylene, ethyl chloride, ethylene dichloride, vinyl chloride, and/or ethane, the overall catalyst chloriding effectiveness value of process 20 can be defined as follows:

$$Z^* = \frac{(ECL + 2*EDC + VCL)}{(C_2H_6 + 0.01*C_2H_4)} \quad (2)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C=CH$—Cl), respectively, in reactor feed stream 22. $C_2H_6$ and $C_2H_4$ are the concentrations in mole percent of ethane and ethylene, respectively, in reactor feed stream 22. It is important that the relative effectiveness of the gaseous chlorine-containing promoter and the hydrocarbon dechlorinating species also be measured under the reaction conditions which are being used in the process. As will be discussed below, Z* is preferably varied as the catalyst ages to compensate for decreases in catalyst activity. However, Z* will preferably be maintained at a level that is no greater than about 20 and which is most preferably no greater than about 15. Z* is preferably at least about 1.

Although the gaseous chlorine-containing promoter may be supplied as a single species, upon contact with the catalyst, other species may be formed leading to a mixture in the gas phase. Consequently, if the reaction gases are recycled such as via recycle stream 18, a mixture of species will be found in the inlet of the reactor. In particular, the recycled reaction gases at the inlet may contain ethyl chloride, vinyl chloride, ethylene dichloride and or methyl chloride, even though only ethyl chloride or ethylene dichloride is supplied to the system. The concentrations of ethyl chloride, vinyl chloride, and ethylene dichloride must be considered in calculating Z*.

The order in which the inlet gases (alkylene, oxygen and ballast gas) and gas phase promoter are mixed together is not critical, and they may be mixed simultaneously or sequentially. The order of mixing of the gaseous components of the process may be chosen for convenience and/or for safety reasons. For example, oxygen is generally added after the ballast gas for reasons of safety. However, the gas phase promoter should be present in reactor feed stream 22 as it is introduced to the solid catalyst in reactor 10.

In the embodiment of FIG. 1, Reactor 10 is a fixed bed reactor. However, any suitable reactor may be used, for example, fixed bed tubular reactors, continuous stirred tank reactors (CSTR), and fluid bed reactors, a wide variety of which are well known to those skilled in the art and need not be described in detail herein. The desirability of recycling unreacted feed, or employing a single-pass system, or using successive reactions to increase ethylene conversion by employing reactors in series arrangement can also be readily determined by those skilled in the art. The particular mode of operation selected is usually dictated by process economics.

The epoxidation reaction is generally exothermic. Thus, a coolant system 28 (e.g., a cooling jacket or a hydraulic circuit with a coolant fluid such as a heat transfer fluid or boiling water) is provided to regulate the temperature of reactor 10. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side. The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature.

The reaction temperature is generally selected to provide the desired yield of ethylene oxide, but as will be seen below, is adjusted to account for catalyst aging. It should be noted that the terms "reaction temperature," "epoxidation temperature" or "epoxidation reaction temperature" refer to any selected temperature(s) that are directly or indirectly indicative of the catalyst bed temperature. In certain embodiments, the reaction temperature may be a catalyst bed temperature at a specific location in the catalyst bed. In other embodiments, the reaction temperature may be a numerical average of several catalyst bed temperature measurements made along one or more catalyst bed dimensions (e.g., along the length). In additional embodiments, the reaction temperature may be the reactor outlet gas temperature. In further embodiments, the reaction temperature may be the reactor coolant outlet temperature. In other embodiments, the reaction temperature may be the reactor coolant inlet temperature.

The epoxidation reaction is carried out at a temperature that is preferably at least about 200° C., more preferably at least about 210° C., and most preferably at least about 220° C. Reaction temperatures of no more than 300° C. are preferred, and reaction temperatures of no more than about 290° C. are more preferred. Reaction temperatures of no more than about 280° C. are most preferred. The reactor pressure is selected based on the desired mass velocity and productivity and ranges generally from about 5 atm (506 kPa) to about 30 atm (3.0 MPa). The gas hourly space velocity (GHSV) is preferably greater than about 3000 $hr^{-1}$, more preferably greater than about 4,000 $hr^{-1}$, and most preferably greater than about 5,000 $hr^{-1}$.

Reactor 10 includes a high efficiency, silver catalyst. Generally, the highly efficient silver based catalyst is a supported catalyst. The support (also known as a "carrier") may be selected from a wide range of inert support materials. Such support materials may be natural or artificial inorganic materials and they include silicon carbide, clays, pumice, zeolites, charcoal and alkaline earth metal carbonates, such as calcium carbonate. Preferred are refractory support materials, such as alumina, magnesia, zirconia and silica. The most preferred support material is a-alumina. In one exemplary embodiment, silver is deposited on the catalyst carrier as are one or more solid promoters, which are discussed further below.

There are many well-known methods of preparing supports suitable for use in ethylene oxide catalysts. Some of such methods are described in, for example, U.S. Pat. Nos. 4,379,134; 4,806,518; 5,063,195; 5,384,302, U.S. Patent Application 20030162655 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity after its removal during the calcination step. The levels of impurities in the finished carrier are determined by the purity of the raw materials used, and their degree of volatilization during the calcination step. Common impurities may include silica, alkali and alkaline earth metal oxides and trace amounts of metal and/or non-metal-containing additives. Another method for preparing a carrier having particularly suitable properties for ethylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina carrier.

There have been employed alumina which has a very high purity, that is, at least 98 wt. % alpha-alumina, any remaining components being silica, alkali metal oxides (for example, sodium oxide) and trace amounts of other metal-containing and/or non-metal-containing additives or impurities. Likewise, there have been employed alumina of lower purity, that is, about 80 wt. % alpha-alumina, the balance being one or more of amorphous and/or crystalline alumina and other alumina oxides, silica, silica alumina, mullite, various alkali metal oxides (for example, potassium oxide and cesium oxide), alkaline earth metal oxides, transition metal oxides (for example, iron oxide and titanium oxide), and other metal and non-metal oxides. In addition, the material used to make the carrier may comprise compounds which have been known for improving catalyst performance, for example, rhenium, (such as rhenates) and molybdenum.

In an especially preferred embodiment, the support material comprises at least about 80 weight percent α-alumina and less than about 30 parts per million acid-leachable alkali metals by weight, the weight percent of the α-alumina and the concentration of the acid-leachable alkali metals being calculated on the weight of the carrier, where the acid-leachable alkali metals are selected from lithium, sodium, potassium, and mixtures thereof.

The alpha-alumina carrier prepared as described hereinabove preferably has a specific surface area of at least about 0.5 m$^2$/g, and more preferably, at least about 0.7 m$^2$/g. The surface area is typically less than about 10 m$^2$/g, and preferably, less than about 5 m$^2$/g. The alpha-alumina carrier preferably has a pore volume of at least about 0.3 cm$^3$/g, and more preferably, from about 0.4 cm$^3$/g to about 1.0 cm$^3$/g and a median pore diameter from about 1 to about 50 microns. A variety of carrier morphologies may be used, including pills, cylinders, cylinders with one or more longitudinal axial openings, chunks, tablets, pieces, pellets, rings, spheres, wagon wheels, saddle rings and toroids having star shaped inner and/or outer surfaces. In a preferred embodiment, the high-purity alpha-alumina preferably includes particles many of which have at least one substantially flat major surface, and having a lamellate or platelet morphology. In a more preferred embodiment the particles approximate the shape of a hexagonal plate (some particles having two or more flat surfaces), at least 50 percent of which (by number) have a major dimension of less than about 50 microns. In a preferred embodiment, the alpha-alumina carrier comprises zirconium silicate (zircon), present substantially as zirconium silicate in the finished carrier, more preferably, in an amount up to about 4 weight percent, calculated on the weight of the carrier.

Catalysts of this invention for the production of alkylene oxide, for example, ethylene oxide or propylene oxide may be prepared with the aforementioned carriers by impregnating the carrier with a solution of one or more silver compounds, depositing the silver throughout the pores of the carrier and reducing the silver compound as is well known in the art. See for example, Liu, et al., U.S. Pat. No. 6,511,938 and Thorsteinson et al., U.S. Pat. No. 5,187,140, incorporated herein by reference.

Generally, the carrier is impregnated with a catalytic amount of silver, which is any amount of silver capable of catalyzing the direct oxidation of the alkylene with oxygen or an oxygen-containing gas to the corresponding alkylene oxide. In making such a catalyst, the carrier is typically impregnated (one or more times) with one or more silver compound solutions sufficient to allow the silver to be supported on the carrier in an amount greater than about 5 percent, greater than about 10 percent, greater than about 15 percent, greater than about 20 percent, greater than about 25 percent, preferably, greater than about 27 percent, and more preferably, greater than about 30 percent by weight, based on the weight of the catalyst. Typically, the amount of silver supported on the carrier is less than about 70 percent, and more preferably, less than about 50 percent by weight, based on the weight of the catalyst.

Although silver particle size in the finished catalyst is important, the preferred range is not narrow. A suitable silver particle size can be in the range of from about 10 to about 10,000 angstroms in diameter. A preferred silver particle size ranges from greater than about 100 to less than about 5,000 angstroms in diameter. It is desirable that the silver be relatively uniformly dispersed within, throughout, and/or on the alumina carrier.

As is known to those skilled in the art, there are a variety of known promoters, that is, materials which, when present in combination with particular catalytic materials, for example, silver, benefit one or more aspect of catalyst performance or otherwise act to promote the catalyst's ability to make a desired product, for example ethylene oxide or propylene oxide. Such promoters in themselves are generally not considered catalytic materials. The presence of such promoters in the catalyst has been shown to contribute to one or more beneficial effects on the catalyst performance, for example enhancing the rate or amount of production of desired product, reducing the temperature required to achieve a suitable rate of reaction, reducing the rates or amounts of undesired reactions, etc. Competing reactions occur simultaneously in the reactor, and a critical factor in determining the effectiveness of the overall process is the measure of control one has over these competing reactions. A material which is termed a promoter of a desired reaction can be an inhibitor of another reaction, for example a combustion reaction. What is significant is that the effect of the promoter on the overall reaction is favorable to the efficient production of the desired product, for example ethylene oxide. The concentration of the one or more promoters present in the catalyst may vary over a wide range depending on the desired effect on catalyst performance, the other components of a particular catalyst, the physical and chemical characteristics of the carrier, and the epoxidation reaction conditions.

There are at least two types of promoters—solid promoters and gaseous promoters. The solid and/or gaseous promoters are provided in a promoting amount. A "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), efficiency, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced efficiency at one set of operating conditions may be operated at a different set of conditions wherein the improvement shows up in the activity rather than the efficiency and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

Examples of well-known solid promoters for catalysts used to produce ethylene oxide include compounds of potassium, rubidium, cesium, rhenium, sulfur, manganese, molybdenum, and tungsten. During the reaction to make ethylene oxide, the specific form of the promoter on the catalyst may be unknown. Examples of solid promoter compositions and their characteristics as well as methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766,105, 4,808,738, 4,820,675, and 4,833,261, all incorporated herein by reference. The solid promoters are generally added as chemical compounds to the catalyst prior to its use. As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions when added as a compound to the catalyst. Once in the catalyst, the form of the promoter is not always known, and the promoter may be present without the counterion added during the preparation of the catalyst. For example, a catalyst made with cesium hydroxide may be analyzed to contain cesium but not hydroxide in the finished catalyst. Likewise, compounds such as alkali metal oxide, for example cesium oxide, or transition metal oxides, for example $MoO_3$, while not being ionic, may convert to ionic compounds during catalyst preparation or in use. For the sake of ease of understanding, the solid promoters will be referred to in terms of cations and anions regardless of their form in the catalyst under reaction conditions.

The catalyst prepared on the carrier may contain alkali metal and/or alkaline earth metal as cation promoters. Exemplary of the alkali metal and/or alkaline earth metals are lithium, sodium, potassium, rubidium, cesium, beryllium, magnesium, calcium, strontium and barium. Other cation promoters include Group 3b metal ions including lanthanide series metals. In some instances, the promoter comprises a mixture of cations, for example cesium and at least one other alkali metal, to obtain a synergistic efficiency enhancement as described in U.S. Pat. No. 4,916,243, herein incorporated by reference. Note that references to the Periodic Table herein shall be to that as published by the Chemical Rubber Company, Cleveland, Ohio, in CRC Handbook of Chemistry and Physics, 46th Edition, inside back cover.

The preferred concentration of the alkali metal promoters in the finished catalyst is not narrow and may vary over a wide range. The optimum alkali metal promoter concentration for a particular catalyst given the other carrier and catalyst properties will be dependent upon performance characteristics, such as catalyst efficiency, rate of catalyst aging and reaction temperature.

The concentration of alkali metal (based on the weight of cation, for example cesium) in the finished catalyst may vary from about 0.0005 to 1.0 wt. %, preferably from about 0.005 to 0.5 wt. %. The preferred amount of cation promoter deposited on or present on the surface of the carrier or catalyst generally lies between about 10 and about 4000, preferably about 15 and about 3000, and more preferably between about 20 and about 2500 ppm by weight of cation calculated on the total carrier material. Cation promoter amounts between about 50 and about 2000 ppm by weight of the total carrier material are frequently most preferable. When the alkali metal cesium cation is used in mixture with other cations, the ratio of cesium to any other alkali metal and alkaline earth metal cation(s), if used, to achieve desired performance is not narrow and may vary over a wide range. The weight ratio of cesium to the other cation promoters may vary from about 0.0001:1 to 10,000:1, preferably from about 0.001:1 to 1,000:1.

Examples of some of the anion promoters which may be employed with the present invention include the halides, for example fluorides and chlorides, and the oxyanions of the elements other than oxygen having an atomic number of 5 to 83 of Groups 3b to 7b and 3a to 7a of the Periodic Table. One or more of the oxyanions of nitrogen, sulfur, manganese, tantalum, molybdenum, tungsten and rhenium may be preferred for some applications.

The types of anion promoters or modifiers suitable for use in the catalysts of this invention comprise, by way of example only, oxyanions such as sulfate, $SO_4^{-2}$/phosphates, for example, $PO_4^{-3}$, titanates, e.g., $TiO_3^{-2}$, tantalates, for example, $Ta_2O_6^{-2}$, molybdates, for example, $MoO_4^{-2}$, vanadates, for example, $V_2O_4^{-2}$, chromates, for example, $CrO_4^{-2}$, zirconates, for example, $ZrO_3^{-2}$, polyphosphates, manganates, nitrates, chlorates, bromates, borates, silicates, carbonates, tungstates, thiosulfates, cerates and the like. The halides may also be present, including fluoride, chloride, bromide and iodide.

It is well recognized that many anions have complex chemistries and may exist in one or more forms, for example, orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. In many instances, analytical techniques may not be sufficient to precisely identify the species present. The invention is not intended to be limited by the exact species that may ultimately exist on the catalyst during use.

With certain highly efficient catalysts, the most preferred promoter comprises rhenium, which can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

Another class of promoters, which may be employed with the present invention, includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, for example permanganate anion, and the like. To stabilize the manganese component in certain impregnating solutions, it may be necessary to add a chelating compound such as ethylenediaminetetraacetic acid (EDTA) or a suitable salt thereof.

The amount of anion promoter may vary widely, for example, from about 0.0005 to 2 wt. %, preferably from about 0.001 to 0.5 wt. % based on the total weight of the catalyst. When used, the rhenium component is often provided in an amount of at least about 1, say, at least about 5, for example, about 10 to 2000, often between 20 and 1000, ppmw calculated as the weight of rhenium based on the total weight of the catalyst.

The promoters for catalysts employing the present invention may also be of the type comprising at least one efficiency-enhancing salt of a member of a redox-half reaction pair which is employed in an epoxidation process in the presence of a gaseous nitrogen-containing component capable of forming a gaseous efficiency-enhancing member of a redox-half reaction pair under reaction conditions. The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213-1218 (1961) or "CRC Handbook of Chemistry and Physics", 65th Edition, CRC Press, Inc., Boca Raton, Fla., pages D155-162 (1984). The term "redox-half reaction pair" refers to the pairs of atoms, molecules or ions or mixtures thereof which undergo oxidation or reduction in such half-reaction equations. Such terms as redox-half reaction pairs are used herein to include those members of the class of substance which provide the desired performance enhancement, rather than a mechanism of the chemistry occurring. Preferably, such compounds, when associated with the catalyst as salts of members of a half reaction pair, are salts in which the anions are oxyanions, preferably an oxyanion of a polyvalent atom; that is, the atom of the anion to which oxygen is bonded is capable of existing, when bonded to a dissimilar atom, in different valence states. As used herein, the term "salt" does not indicate that the anion and cation components of the salt be associated or bonded in the solid catalyst, but only that both components be present in some form in the catalyst under reaction conditions. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The salt of a member of a redox-half reaction pair is added to the catalyst in an amount sufficient to enhance the efficiency of the epoxidation reaction. The precise amount will vary depending upon such variables as the gaseous efficiency-enhancing member of a redox-half reaction used and concentration thereof, the concentration of other components in the gas phase, the amount of silver contained in the catalyst, the surface area of the support, the process conditions, for example space velocity and temperature, and morphology of support. Alternatively, a suitable precursor compound may also be added such that the desired amount of the salt of a member of a redox-half reaction pair is formed in the catalyst under epoxidation conditions, especially through reaction with one or more of the gas-phase reaction components. Generally, however, a suitable range of concentration of the added efficiency-enhancing salt, or precursor thereof, calculated as cation, is about 0.01 to about 5%, preferably about 0.02 to about 3%, by weight, based on the total weight of the catalyst. Most preferably the salt is added in an amount of about 0.03 to about 2%, by weight.

The preferred gaseous efficiency-enhancing members of redox-half reaction pairs are compounds containing an element capable of existing in more than two valence states, preferably nitrogen and another element which is, preferably, oxygen. The gaseous component capable of producing a member of a redox-half reaction pair under reaction conditions is a generally a nitrogen-containing gas, such as for example nitric oxide, nitrogen dioxide and/or dinitrogen tetroxide, hydrazine, hydroxylamine or ammonia, nitroparaffins (for example, nitromethane), nitroaromatic compounds (for example nitrobenzene), N-nitro compounds, and nitriles (for example, acetonitrile). The amount of nitrogen-containing gaseous promoter to be used in these catalysts is that amount sufficient to enhance the performance, such as the activity of the catalyst and particularly the efficiency of the catalyst. The concentration of the nitrogen-containing gaseous promoter is determined by the particular efficiency-enhancing salt of a member of a redox-half reaction pair used and the concentration thereof, the particular alkene undergoing oxidation, and by other factors including the amount of carbon dioxide in the inlet reaction gases. For example, U.S. Pat. No. 5,504,053 discloses that when the nitrogen-containing gaseous promoter is NO (nitric oxide), a suitable concentration is from about 0.1 to about 100 ppm, by volume, of the gas stream.

Although in some cases it is preferred to employ members of the same half-reaction pair in the reaction system, that is, both the efficiency-enhancing salt promoter associated with the catalyst and the gaseous promoter member in the feedstream, as, for example, with a preferred combination of potassium nitrate and nitric oxide, this is not necessary in all cases to achieve satisfactory results. Other combinations, such as $KNO_2/N_2O_3$, $KNO_3/N_2O_2$, $KNO_3/N_2O_4$, $KNO_2/NO$, $KNO_2/NO_2$ may also be employed in the same system. In some instances, the salt and gaseous members may be found in different half-reactions which represent the first and last reactions in a series of half-reaction equations of an overall reaction.

Depending on the composition of the solid catalyst being employed, one or more gaseous components capable of generating at least one efficiency-enhancing member of a redox half reaction pair may be employed as gaseous promoters, as is well known in the art. The preferred gaseous component capable of generating an efficiency-enhancing member of a redox half reaction pair is preferably a nitrogen-containing component. See, for example, Liu, et al., U.S. Pat. No. 6,511,938 particularly at column 16, lines 48 through 67 and column 17, line 28, and Notermann, U.S. Pat. No. 4,994,589, particularly at column 17, lines 10-44, each incorporated herein by reference. As used herein, the term "salt" does not indicate that the anion and cation components of the salt be associated or bonded in the solid catalyst, but only that both components be present in some form in the catalyst under reaction conditions.

Alternatively, a suitable precursor compound may also be added such that the desired amount of the salt of a member of a redox-half reaction pair is formed in the catalyst under epoxidation conditions, especially through reaction with one or more of the gas-phase reaction components. The suitable range of concentration of the precursor of the efficiency enhancing promoter is the same as for the salt.

It is desirable that the silver and one or more solid promoters be relatively uniformly dispersed on the carrier. A preferred procedure for depositing silver catalytic material and one or more promoters comprises: (1) impregnating a carrier according to the present invention with a solution comprising a solvent or solubilizing agent, silver complex and one or more promoters, and (2) thereafter treating the impregnated carrier to convert the silver compound and effect deposition of silver and the promoter(s) onto the exterior and interior pore surfaces of the carrier. Silver and promoter depositions are generally accomplished by heating the solution containing carrier at elevated temperatures to evaporate the liquid within the carrier and effect deposition of the silver and promoters onto the interior and exterior carrier surfaces. The temperature of the heating step is high enough to reduce any silver compounds to metallic silver. Impregnation of the carrier is the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

Well known methods can be employed to analyze for the amounts of silver and solid promoters deposited onto the alumina carrier. The skilled artisan may employ, for example, material balances to determine the amounts of any of these deposited components. Alternatively, any suitable analytical technique for determining elemental composition, such as X-ray fluorescence (XRF), may be employed to determine the amounts of the deposited components.

As is known in the art, as a reaction is carried out over a catalyst over a period of time, the catalyst eventually begins to "age" and lose activity, which typically means that the number of active sites available for catalyzing the desired reaction are reduced. The reaction temperature is typically increased to increase the reaction rate and offset the decline in activity, without making substantial changes in the gas-phase promoter concentration. For conventional catalysts, this approach is typically acceptable because the catalyst optimum promoter concentration is substantially invariant with reaction temperature (i.e., the change in optimum promoter concentration with respect to a change in reaction temperature is relatively small. Therefore, catalyst efficiency does not suffer significantly by changing temperature without a concomitant change in gas-phase promoter concentration). However, with high efficiency catalysts of the type described herein, optimum efficiency is temperature dependent. In addition, the relationship between efficiency and overall chloriding effectiveness (i.e., the efficiency vs. effectiveness curve) is temperature dependent. Moreover, reaction rate is a function of chloriding level. Thus, certain processes such as those described in U.S. Pat. No. 7,193,094 utilize the simultaneous manipulation of reaction temperature and gas-phase promoter concentration. However, this approach introduces complexity into the operation and control of the process and can cause or exacerbate the effect of process disturbances.

Figure 2:
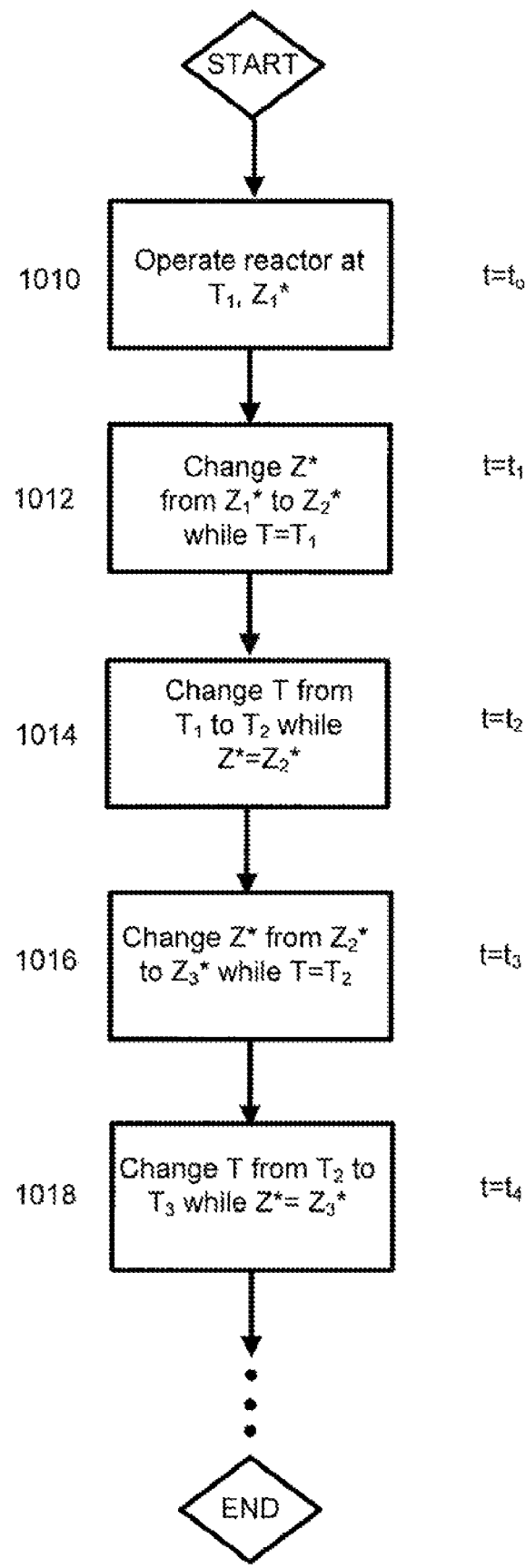
FIG. 2 is a flow chart depicting an embodiment of a simplified method for operating the process of FIG. 1.

It has been discovered that if changes in overall chloriding effectiveness are maintained within certain values, the relationship between the efficiency to alkylene oxide and the effectiveness is relatively flat whereas the reaction rate changes monotonically with changes in gas phase chloriding level. As a result, alternating changes in gas phase promoter concentration and reaction temperature can be made to compensate for activity decreases without substantially impacting efficiency. The changes are preferably made while holding the reactor inlet alkylene concentration at a substantially constant value. Referring to FIG. 2, a flow chart depicting a simplified method of operating an alkylene oxide production process with an aging, high efficiency catalyst is described. In accordance with the method, reactor 10 is operated at an initial temperature $T_1$ and an initial overall chloriding effectiveness $Z_1^*$ (step 1010). In a preferred embodiment, $T_1$ and $Z_1^*$ are chosen to provide the maximum efficiency at the desired rate of ethylene oxide production. As the catalyst ages, the yield of alkylene oxide will eventually begin to decline. If the feed rate, pressure, and composition have not changed, the mole percentage of alkylene oxide in reactor outlet stream 24 and the yield of alkylene oxide will decline. Thus, at a time $t_1$ the overall chloriding effectiveness is increased from $Z_1^*$ to $Z_2^*$ (e.g., by increasing the flow of ethyl chloride in gas phase promoter feed stream 14 or by decreasing the concentration of ethane or other dechloriding components in the reactor feed) while maintaining the reaction temperature at $T_1$ (step 1012), and preferably, while holding the concentration of alkylene in the reactor feed at a substantially constant value. The change in $Z^*$ will increase the rate of reaction, tending to increase the alkylene oxide yield, while at most producing a slight decrease in efficiency, which is preferably no more than 0.5 percentage points, more preferably no more than 0.4 percentage points, and most preferably no more than 0.3 percentage points. The process is maintained at $T_1$ and $Z_2^*$ until a time $t_2$ when a further decrease in catalyst activity is observed (e.g., as manifested by a decrease in reactor effluent alkylene oxide concentration and/or in alkylene oxide yield). At a time $t_2$, the reaction temperature T is increased from $T_1$ to $T_2$ (e.g., by reducing the flow rate of coolant in cooling circuit 28 or by increasing the steam drum pressure in a boiling water cooled system) while the overall catalyst chloriding effectiveness is maintained at $Z_2^*$ (step 1014). The increase in reaction temperature will increase the rate of reaction (tending to increase the alkylene oxide yield), while at most producing a slight decrease in efficiency which is preferably no more than 0.5 percentage points, more preferably no more than 0.4 percentage points, and most preferably no more than 0.3 percentage points.

As the process continues to operate, the catalyst continues to age. At a time $t_3$, a further decrease in catalyst activity is observed, and the overall chloriding effectiveness value is increased from $Z_2^*$ to $Z_3^*$ while the reaction temperature is maintained at $T_2$ (step 1016). Again, the reaction rate increases while efficiency decreases by no more than the amounts described above for the change in $Z^*$ made at $t_1$. After a further decline in activity, at time $t_4$, the reaction temperature is increased from $T_2$ to $T_3$ while $Z^*$ is maintained at $Z_3^*$. The process of alternating $Z^*$ and T in response to activity changes is generally carried out until a process limitation (e.g., the reaction temperature is at its maximum allowable limit) is reached and the desired yield of alkylene oxide can no longer be obtained, or the efficiency is uneconomically low. At that point, reactor 10 is shut down and the catalyst is replaced or regenerated.

The time intervals (i.e., periods) between changes in $Z^*$ or T (i.e., $t_2$-$t_1$, $t_3$-$t_2$) may be the same or different. In addition, they may be pre-selected or may be dictated by other process changes indicative of catalyst activity decreases. In one preferred embodiment, the concentration of alkylene oxide in reactor outlet stream 24 and/or the yield of alkylene oxide is determined, and changes in the concentration and/or yield are used to determine when to change $Z^*$ or T. In accordance with the embodiment, the observed changes in alkylene oxide concentration used to determine when to change T and $Z^*$ are preferably less than about 0.5 mole percent, more preferably less than about 0.4 mole percent, and most preferably less than about 0.3 mole percent. The observed changes in alkylene oxide concentration used to determine when to change T or $Z^*$ are preferably greater than 0 mole percent, more preferably greater than about 0.1 mole percent, and most preferably greater than about 0.2 mole percent.

The time intervals $t_2$-$t_1$, $t_3$-$t_2$, etc. may also be selected based on catalyst aging. One measure of catalyst aging is the total production of alkylene oxide on a mass basis (e.g., using metric kilotons "kt") divided by the catalyst-packed reactor volume (e.g., in cubic meters) in reactor 10. Another measure of catalyst aging is the total production of alkylene oxide on a molar basis divided by the catalyst-packed reactor volume. In accordance with this embodiment, changes in $Z^*$ and T are made in an alternating sequence at catalyst aging intervals that may be the same or different. On a mass basis, the catalyst aging intervals used to determine when to change either T or $Z^*$ are preferably less than about 1.5 kt alkylene oxide/$m^3$ catalyst, more preferably less than about 1.0 kt alkylene oxide/$m^3$ catalyst, even more preferably less than about 0.5 kt alkylene oxide/$m^3$ catalyst, and still more preferably less than about 0.25 kt alkylene oxide/$m^3$ catalyst. The catalyst aging intervals are preferably greater than about 0.05 kt alkylene oxide/$m^3$ catalyst, 0.1 kt alkylene oxide/$m^3$ catalyst, and more preferably greater than about 0.2 kt alkylene oxide/$m^3$ catalyst. The total catalyst age at the end of run is preferably less than about 10 kt alkylene oxide/$m^3$ catalyst, more preferably less than about 8 kt alkylene oxide/$m^3$ catalyst, and most preferably less than about 5 kt alkylene oxide/$m^3$ catalyst.

In the paragraph above, the time interval is expressed in terms of cumulative production of alkylene oxide, commonly reported in units of kt/$m^3$, rather than in actual units of time, such as days. The cumulative production can be readily calculated from normal process variables. To calculate the cumulative production, it is necessary to know the volume of the catalyst, the flow rate of process gases over the catalyst corrected to standard conditions, the amount of alkylene oxide produced per pass (conversion), the molecular weight of the specific alkylene oxide being produced, and the time of operation at these conditions. Since some of these variables may change over time, either due to normal process variations, or an intentional change in reactor operating conditions, it is common to calculate the cumulative production for a series of relatively short periods, during which conditions are essentially constant, such as an hour, and then sum the cumulative production for each of these shorter periods to obtain the total cumulative production.

The changes in $Z^*$ and T described in FIG. 2 are generally of a magnitude that is sufficient to increase the rate of reaction to the extent needed to obtain a desired yield (and/or effluent concentration) of alkylene oxide. The increments in $Z^*$ and T may be the same or different at the various time intervals $t_2$-$t_1$, $t_3$-$t_2$, etc. The changes in either variable may be made as step changes, or they may be linear or non-linear with respect to time or catalyst age. However, the magnitude of the change in $Z^*$ at any given interval is preferably less than about 5, more preferably less than about 3, still more preferably less than about 2, even more preferably less than about 1, and most preferably no more than about 0.5. The magnitude of the change in reaction temperature at any given interval is preferably less than about 15° C., more preferably less than about 10° C., and most preferably less than about 5° C. The efficiency of the process for alkylene oxide is preferably greater than 85.7%. The end of run efficiency is preferably no less than about 80%. The concentration of alkylene oxide in reactor outlet stream 24 over the run of the catalyst is preferably at least about 1.0 mole percent, more preferably at least about 1.5 mole percent, and most preferably at least about 2.0 mole percent. The concentration of alkylene oxide in reactor product stream 24 is preferably no more than about 6.0 mole percent and more preferably not more than about 4.0 mole percent.

Figure 3:
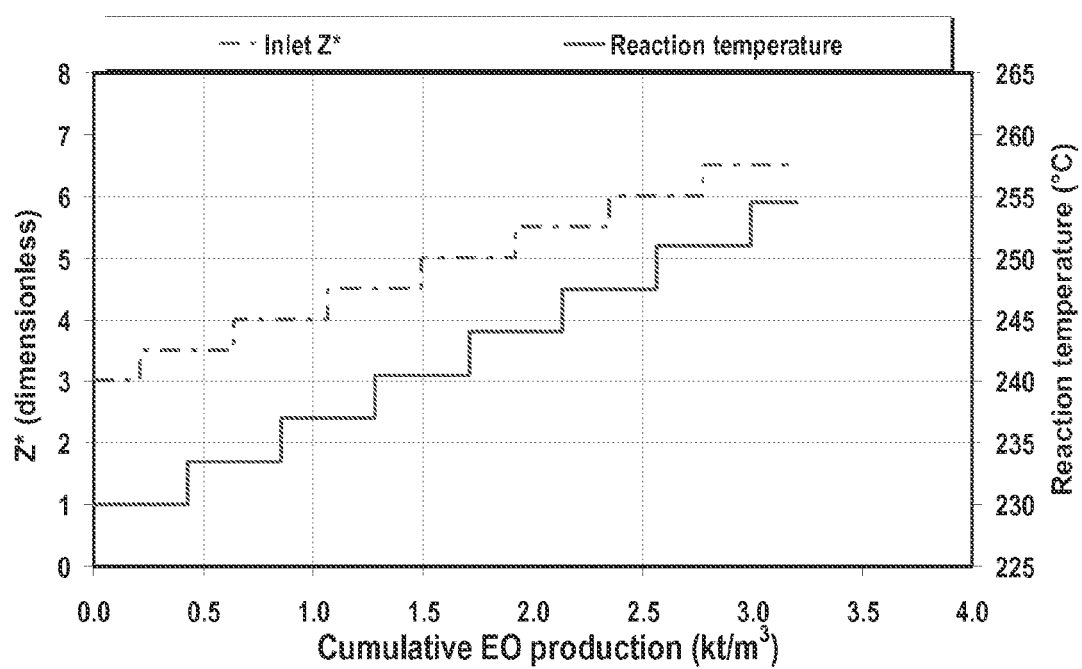
FIG. 3 is a graph depicting alternate step changes in an overall catalyst chloriding effectiveness parameter and reaction temperature for a process of making ethylene oxide by epoxidizing ethylene.

Referring to FIG. 3, an exemplary illustration of a simplified method of producing ethylene oxide by reacting ethylene, oxygen, and an ethyl chloride gas phase promoter over a high efficiency catalyst is provided. The upper graph is the overall chloriding effectiveness, $Z^*$, and the lower graph is the reaction temperature. The catalyst is a high efficiency, rhenium-promoted silver catalyst of the type described previously. The x-axis represents the age of the catalyst expressed as cumulative production of ethylene oxide divided by the catalyst volume in kt/$m^3$.

As indicated in the figure, fresh catalyst is provided and the reaction is initially conducted at a temperature of 230° C. and an overall chloriding effectiveness value, $Z^*$, of 3.0. In one embodiment, the initial conditions are selected to provide an optimal condition at which the efficiency to ethylene oxide is at a maximum for the desired rate of production of ethylene oxide. After the catalyst has produced about 0.21 kt ethylene oxide/m³ catalyst, a decline in ethylene oxide yield (and/or effluent ethylene oxide concentration) is observed, and Z* is increased from 3.0 to 3.5 while the reaction temperature is held at 230° C. and the reactor inlet ethylene concentration is held constant. This change restores the yield of ethylene oxide while moving Z* slightly away from its optimum (efficiency-maximizing) value. Nevertheless, because of the range in which Z* is operated, the efficiency change is relatively small.

After an additional period of time elapses, the catalyst ages by an additional 0.21 kt ethylene oxide/m³ catalyst, and a decline in ethylene oxide yield and/or effluent ethylene oxide concentration is observed. At this point, the reaction temperature is increased from about 230° C. to about 233.5° C., thereby restoring the ethylene oxide yield. This change causes the relationship between efficiency and Z* to change such that the Z* is either at or slightly below its optimum value. However, because of the range in which Z* is operated, the efficiency change is again relatively small.

The process of alternating changes in reaction temperature and Z* continues as shown in FIG. 3 until the catalyst reaches end of run at about 3.2 kt ethylene oxide/m³ catalyst. As FIG. 3 indicates, seven (7) changes in Z* are made, each comprising a step change of about 0.5. Similarly, seven (7) changes in reaction temperature are made, each comprising a step change of about 3.5° C. In FIG. 3, the alternate changes are made at uniform increments of catalyst age (i.e., about 0.21 kt ethylene oxide/m³), and the magnitude of the reaction temperature and Z* steps are constant throughout the run. However, the catalyst age increments may be varied as may the magnitude of the step changes. In addition, while Z* is varied first in FIG. 3, the reaction temperature could instead be varied first.

Figure 4:
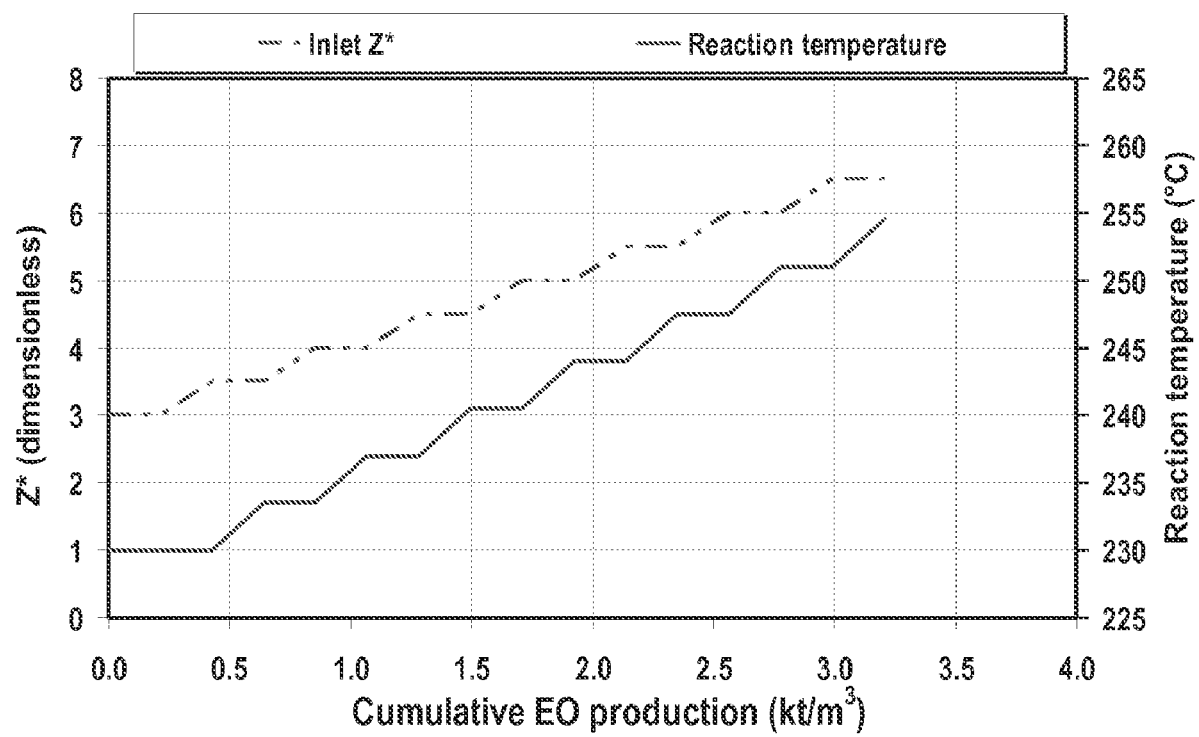
FIG. 4 is a graph depicting alternate ramp (linear) changes in an overall catalyst chloriding effectiveness parameter and reaction temperature for a process of making ethylene oxide by epoxidizing ethylene.

In FIG. 3, the alternating changes in Z* and reaction temperature are made as step changes. However, the changes may be made more gradually in dynamically different ways, such as by linearly varying Z* and reaction temperature with respect to time and/or catalyst age or by varying them non-linearly with respect to time and/or catalyst age. Referring to FIG. 4, another method of making alternating changes in Z* and reaction temperature is depicted. In FIG. 4, the upper graph is Z* and the lower graph is reaction temperature. As in the method of FIG. 3, with fresh catalyst in reactor 10, the initial reaction conditions are chosen to provide the maximum efficiency at the desired ethylene oxide yield. After the catalyst ages to about 0.21 kt ethylene oxide/m³ catalyst, a decline in ethylene oxide yield is observed. At this point, Z* is gradually increased (e.g., by increasing the flow rate of ethyl chloride in gas phase promoter feed stream 14 or by decreasing the concentration of ethane or other dechloriding components in the reactor feed) in a manner that varies linearly with catalyst age while the reaction temperature is held constant at its initial value of 230° C. The concentration of the alkylene is preferably held at a substantially constant value. The first change in Z* is about 0.5 and is made over a catalyst age period of about 0.21 kt ethylene oxide/m³ catalyst, yielding a slope (A Z*/A age) of about 2.4 m³ catalyst/kt ethylene oxide.

Once a catalyst age of about 0.42 kt ethylene oxide/m³ catalyst is reached, the reaction temperature is increased from 230° C. to about 233.5° C. over a catalyst age period of about 0.21 kt ethylene oxide/m3 catalyst while Z* is held constant at about 3.5, yielding a slope, (ΔT/Δage) of about 16.7° C.*m³ catalyst/kt ethylene oxide. At that point, Z* is increased by another 0.5 over a period of 0.21 kt ethylene oxide/m³ catalyst while the reaction temperature is held constant at about 233.5° C. The process is continued until the catalyst reaches end of run at about 3.2 kt/m³. In FIG. 4, once a change in one variable (T or Z*) is completed, increases in the other variable are initiated at substantially the same time. However, the process could be carried out so that neither Z* nor reaction temperature are changed for a period of time between initiating changes in the variables. In addition, the rate of change of either variable, or the overall extent of each change, could be varied during the catalyst run, as could the intervals between changes.

As discussed previously, in addition to an organic chloride gas phase promoter, one or more gaseous components capable of generating at least one efficiency-enhancing member of a redox half reaction pair may be employed as a gas phase promoters. In certain preferred embodiments, both a nitrogen-containing gas phase promoter and an organic chloride gas phase promoter are used.

Without wishing to be bound by any particular theory, it is believed that the gaseous nitrogen-containing promoter, when introduced to a reactor with gaseous chlorine-containing promoter, the solid catalyst, and other raw materials, such as alkylene and oxygen, improves the overall performance of the catalyst by affecting the amount of nitrogen-containing species on the catalyst surface which directly affects the efficiency of the catalyst. As mentioned previously, chlorine-containing species also enhance efficiency. Both species have an optimum concentration determined by the balance between the promoting effect on efficiency and/or activity and/or stability, the blockage of sites for reaction, and the enhancement or inhibition of secondary reactions between the various species present in the system. In addition, however, it is believed that the existence of these secondary reactions results in a correlation between the optimum of the gaseous nitrogen-containing promoter and the chlorine-containing promoter for catalysts comprising an efficiency-enhancing salt of a member of a redox-half reaction pair. Thus, it has been found that the volume ratio of the nitrogen-containing gas phase promoter to the organic chloride gas phase promoter may have a significant impact on the performance of a given system. Moreover, the effective amount (the amount that actually participates in the reactions in the catalyst during the process of making ethylene oxide) of the gaseous promoters is not necessarily the same as the actual amount of promoter introduced into the inlet feed. For example, the effective amount of nitrogen-containing efficiency enhancing gas phase promoters depends on the pressure, amount of carbon dioxide, operating temperature and catalyst properties such as catalyst age. In addition, the different compounds which may be used as a gaseous promoter have differing levels of effectiveness.

The effectiveness of a particular gaseous nitrogen-containing promoter is determined by its ability to generate the active nitrogen and oxygen-containing members of a redox half reaction pair in the catalyst. As a result, it is preferred to determine experimentally the effectiveness of the gaseous promoter to be used in the process. For nitrogen-containing efficiency-enhancing gaseous promoters, nitric oxide (NO) is used as the standard compound against which the relative effectiveness of other nitrogen-containing compounds is measured. The reactor pressure also has an impact on the effectiveness of the nitrogen-containing promoters and must therefore be taken into consideration. A variable, N*, may be defined as a measure of the overall effectiveness of the nitrogen-containing promoters:

$$N^*=\text{nitric oxide equivalent(ppmv)}(P_{inlet}/2300 \text{ kPa}) \qquad (3)$$

where $P_{inlet}$ is the absolute pressure at the reactor inlet in kilo Pascals.

If NO is the only gaseous nitrogen-containing promoter present in the reactor inlet, N* is the inlet NO concentration in ppmv multiplied by the inlet pressure in kilo Pascals, absolute, divided by 2300 kPa. When another nitrogen-containing promoter is used alone or in conjunction with NO, the nitric oxide equivalent is the concentration of NO in ppmv plus the concentration of the other gaseous nitrogen-containing promoter (corrected for its effectiveness as a promoter as compared to NO) times the inlet pressure in kilo Pascals, absolute, divided by 2300 kPa. The relative effectiveness of a non-NO promoter can be measured experimentally by replacing NO with the other promoter and determining the concentration needed to obtain the same level of catalyst performance provided by NO. As a way of further illustration, if the required concentration of $NH_3$ at the reactor inlet is 1.5 ppmv to realize equivalent effectiveness in terms of catalyst performance provided by 1 ppmv NO, then the nitric oxide equivalent for 1 ppmv $NH_3$ would be 0.67 ppmv NO. For a hypothetical feed of 1 ppmv $NH_3$ and 1 ppmv NO, N* would then be (1+0.67 ppmv) times the inlet pressure in kilo Pascals, absolute, divided by 2300 kPa. In determining the relative effectiveness of gaseous nitrogen-containing promoters, it is necessary to use the same inlet conditions as those which will be used in the process to make ethylene oxide because the relative effectiveness may be somewhat dependent on the concentrations of the other gases in the feed and temperature.

While Z* is dependent on the concentration of particular hydrocarbons present in the feed gas, N* does not depend on the concentration of hydrocarbon species in the reactor within the ranges specified. Without wishing to be bound by any particular theory, it is believed that the hydrocarbon species are less effective in removing the nitrogen-containing species present on the catalyst surface as compared to their effectiveness in removing the chlorine-containing species present on the catalyst surface.

When using both an organic chloride and a nitrogen-containing gas phase promoter, it is preferred to optimize the inlet concentrations of both gaseous promoters. The concentrations may be chosen to optimize one or more of the following catalyst performance measures: efficiency, activity (temperature), efficiency aging or activity (temperature) aging. Thus, several optima may exist depending on which aspects of catalyst performance have the greatest value to the user. The optimum performance of the catalyst has been found to depend on both gaseous promoter concentrations, that is, some promoter combinations lead to much higher efficiency, activity, or slower aging than others. In a preferred embodiment, the ratio of N*/Z* is less than or equal to about 1. However, for catalysts at the beginning of life with average carbon dioxide concentrations of less than about 1 percent, N*/Z* ranging from about 0.1 to about 0.6 is preferred, particularly for high absolute efficiency and low efficiency aging of the catalyst. For older catalysts which have produced more than 70,000 pounds of ethylene oxide per cubic foot of catalyst (1.1 $kt/m^3$), a N*/Z* ratio of from about 0.4 to about 1.0 is preferred for high efficiency and lower efficiency aging.

In a modified version of the embodiment of FIG. 2, the ratio of N*/Z* is selected based on the foregoing considerations and is maintained as Z* is increased. Thus, in one implementation, a pre-selected ratio of N*/Z* is selected and is used to determine the concentration (and flow rate) of the nitrogen-containing promoter into reactor 10. N* is then set at an initial value, $N_1$*, such that $N_1$*/$Z_1$* equals the pre-selected ratio (e.g., 1.0). In step 1012, Z* is changed from $Z_1$* to $Z_2$*. Is a result, N* is then changed to $N_2$* such that $N_2$*/$Z_2$*=$N_1$*/$Z_1$*=the pre-selected ratio. N* is further adjusted in correspondence with subsequent adjustments to Z* to maintain the pre-selected ratio. As mentioned previously, the pre-selected ratio of N*/Z* may be adjusted during the reactor run as desired. However, in general, changes in Z* will be accompanied by corresponding changes in N* to achieve some pre-selected ratio.

The methods described herein can be used in open loop or closed loop processes. In one example of a closed loop system, depicted in FIG. 1, a controller 26 is provided which receives inputs from an effluent concentration analyzer 27 on reactor outlet stream 24, a reactor feed concentration analyzer 42, an olefin feed flow meter 40, a gas phase promoter feed flow meter 44, and a net product flow meter 52. Controller 26 is preferably implemented in a computerized control system and also includes a CPU and a memory as well as outputs that are ultimately used to adjust control valves 30 and 38. Based on the received inputs, controller 26 determines the mole percentage of alkylene oxide in the reactor effluent 24 and an overall chloriding effectiveness (e.g., Z*) for reactor feed 22.

Controller 26 also receives concentration data for chlorinated hydrocarbons such as ethyl chloride, vinyl chloride, and ethylene dichloride in reactor feed stream 22 from analyzer 42, as well as for the concentration of ethylene, ethane, and any other non-chlorinated hydrocarbons in reactor feed stream. The concentration data is then used to calculate the overall chloriding effectiveness (e.g., Z*). Controller 26 may also receive a user entered set-point for the mole percent of alkylene oxide in reactor effluent 24 and/or the yield of alkylene oxide. Based on the user entered set point and data from analyzer 27, controller 26 determines if the concentration of alkylene oxide in effluent 24 and/or the yield of alkylene oxide is within a pre-determined range of the user entered setpoint. When the alkylene oxide concentration and/or yield falls outside of the pre-determined range, controller 26 either adjusts the reaction temperature or the flow rate of the gas phase promoter (to change Z*) in the alternating manner described previously. To adjust the flow rate of the gas phase promoter, controller 26 resets the set point of gas phase promoter flow controller 36, which receives flow data from flow meter 44 and manipulates control valve 38 to control the flow. To adjust the reaction temperature, controller 26 adjusts the set point of reaction temperature controller 34. Reaction temperature controller 34 receives a temperature signal from a reactor thermocouple and provides an output that resets the set point of coolant flow controller 32 (or the set point of a steam drum pressure controller in a boiling water cooled system). Coolant flow controller 32 receives coolant flow data from flow meter 31 and adjusts coolant control valve 30 to change the coolant flow rate and effect the temperature change.

As shown in FIG. 1, analyzer controller 50 may also be provided to regulate the olefin concentration in reactor feed 22. In the illustrated example, analyzer controller 50 receives compositional data from analyzer 42 indicating the amount of olefin in reactor feed 22. Analyzer controller 50 (which may have a user-entered set point for the olefin concentration in reactor feed stream 22) then resets the set point of flow controller 51 which receives flow data from flow meter 40 and manipulates control valve 12 to control the flow of fresh olefin feed. Analyzer controller 19 receives compositional data from analyzer 42 (or a separate analyzer) indicating the amount of oxygen in reactor feed 22. Analyzer controller 19 then resets the set point of oxygen flow controller 17 (which may be an air flow controller) which receives data from oxygen flow meter 21. Controllers 17, 19, 32, 34, 36, and 50 may be analog or digital and may be implemented in a computerized distributed control system. The illustrated control scheme is merely exemplary and is not meant to limit the scope of the present invention.

The methods used herein may be embodied in a set of computer readable instructions that are stored on a computer readable medium such as a magnetic disk or computer hard drive for use by controller 26. Controller 26 may be implemented in a number of ways, but the use of a computer control system is preferred.

Example 1

A laboratory tubular reactor is charged with a high efficiency, rhenium-promoted silver catalyst that is aged between 100 and 135 days of operation. A feed comprising ethylene, oxygen, and ethyl chloride is fed to the reactor, and the concentration of ethylene oxide in the reactor effluent is determined. More specifically, 0.75 g of a 30-50 mesh Rhenium-promoted high efficiency catalyst is loaded in a micro reactor comprising a 3.05 mm inner diameter stainless steel tube. The reactor is initially operated at the following daily average reactor inlet composition: $8.8 \pm 0.1$ mole percent $O_2$, $34.3 \pm 0.3$ mole percent $C_2H_4$, $0.61 \pm 0.1$ mole percent $C_2H_6$, $1.51 \pm 0.02$ mole percent $CO_2$, and the balance $N_2$. The daily average reactor pressure is $1345 \pm 20$ kPa (absolute), and the feed mixture flow rate is $157.4 \pm 0.8$ standard cc per minute (referenced at 0° C. and 1 atm).

The corresponding $Z^*$ is $6.1 \pm 0.2$ at $5.9 \pm 0.2$ ppmv ethyl chloride. The effects of alternating changes in overall chloriding effectiveness ($Z^*$) and reaction temperature on efficiency (efficiency) and the concentration of ethylene oxide in the effluent are observed. The efficiency can be determined by measuring the inlet and outlet ethylene and ethylene oxide concentrations and using these values to calculate the percentage of the ethylene which is converted to ethylene oxide. However, in certain commercial processes, it can be difficult to accurately obtain a direct measurement of ethylene consumption. Thus, in the method that follows, the increase in the amount of ethylene oxide and carbon dioxide is used to indirectly determine the amount of ethylene consumed.

In the gas phase production of ethylene oxide, there is a loss in the total number of moles for each mole of ethylene oxide that is produced due to the stoichiometry of the reaction. To account for this loss, a "shrink factor" (SF) is calculated as follows:

$$SF = (200 + \% EO \text{ inlet})/(200 + \% EO \text{ outlet}) \quad (4)$$

wherein "% EO inlet" is the mole percentage of ethylene oxide at the reactor inlet and "% EO outlet" is the mole percentage of ethylene oxide at the reactor outlet. Based on the shrink factor, the change in ethylene oxide concentration ($\Delta EO$) is calculated as follows:

$$\Delta EO = SF^* (\% EO \text{ outlet}) - \% EO \text{ inlet} \quad (5)$$

The change in carbon dioxide concentration is calculated as follows:

$$\Delta CO_2 = SF^* (\% CO_2 \text{ outlet}) - \% CO_2 \text{ inlet} \quad (6)$$

wherein "% $CO_2$ outlet" is the mole percentage of $CO_2$ at the reactor outlet and "% $CO_2$ inlet" is mole percentage of $CO_2$ at the reactor inlet. The efficiency is then calculated as follows:

$$\text{Efficiency} = [\Delta EO/(\Delta EO + 0.5^* \Delta CO_2)]^*100 \quad (7)$$

The denominator of equation (7) reflects the fact that each mole of ethylene oxide produced corresponds to one mole of ethylene that is consumed while each mole of carbon dioxide produced corresponds to 0.5 moles of ethylene consumed. Thus, the denominator of equation (7) effectively represents the amount of ethylene consumed, and the numerator effectively represents the amount of ethylene oxide produced.

FIG. 5A depicts the reaction temperature (upper graph, left scale) and inlet $Z^*$ (lower graph, right scale) as a function of catalyst age, which is represented by days of catalyst operation. FIG. 5B depicts efficiency data (upper graph, left scale) and the mole percentage of ethylene oxide in the reactor effluent (lower graph, right scale) for the reaction temperatures and $Z^*$ values shown in FIG. 5A. As FIGS. 5A and 5B indicate, for the first five days of operation (i.e., from catalyst age 100 days to 105 days), the reaction temperature is about 244° C.-245° C., and the overall chloriding effectiveness value, $Z^*$, is about 6.0-6.4. At this point, the concentration of ethylene oxide in the reactor effluent is from about 1.3-1.35 mole percent while the efficiency is from about 88.5% to about 88.8%.

At about day 107, the reaction temperature is increased by about 5° C. while $Z^*$ remains substantially constant. As a result, the concentration of ethylene oxide in the reactor effluent increases to about 1.5 mole percent. The efficiency declines slightly to between about 88.0-88.4%. The decline in efficiency is small due to the relatively flat response of efficiency to $Z^*$ in the range of $Z^*$ values employed. Thus, the increase in reaction temperature increases the yield of ethylene oxide while having only a small effect on efficiency.

As shown in FIG. 5B, as the catalyst continues to age, the concentration of ethylene oxide in the reactor effluent and/or the ethylene oxide yield begins to decline, ultimately reaching a value of about 1.3 mole percent at about day 132. To increase the reaction rate, the overall chloriding effectiveness value $Z^*$ is increased to about 7.0 (FIG. 5A) while holding the reactor inlet ethylene concentration constant. As a result, the concentration of ethylene oxide in the reactor effluent increases to about 1.42 mole percent. The catalyst efficiency slightly increases to about 89% as a result of the change. The reactor is operated at the new temperature and $Z^*$ until the ethylene oxide concentration in the reactor effluent (or the ethylene oxide yield) decreases to a point where further adjustments are required, at which time the reaction temperature is again increased. This example illustrates that reaction temperature and overall chloriding effectiveness can be varied in an alternating manner to achieve a desired ethylene oxide yield while avoiding substantial efficiency losses.

Example 2

A pilot plant, tubular reactor is charged with a high efficiency, rhenium promoted silver catalyst. A feed comprising ethylene, ethyl chloride, and oxygen is fed to the reactor. After reaching steady state operation, the feed composition is: 8.5 mole percent $O_2$, 1.5 mole percent $CO_2$, 40 mole percent $C_2H_4$, 0.6 mole percent $C_2H_6$, 2.5 ppmv ethyl chloride, and the balance $N_2$. The corresponding overall chloriding effectiveness value $Z^*$ is 2.5. The reactor inlet pressure is 295 psig. The reaction temperature (measured as the inlet coolant temperature) is 231° C., and the inlet gas hourly space velocity is 5400 $h^{-1}$. Temperature, gas phase promoter concentration (Inlet ECL), effluent ethylene oxide concentration, $\Delta EO$ (as defined above), and efficiency data are collected at three subsequent catalyst age intervals (represented by the "Days on Stream" column in Table 1). Efficiency values are calculated based on equations (4)-(7) set forth above.

TABLE 1

|  | Days on stream | T (° C.) | Inlet ECL ppmv | ΔEO (mole %) | Efficiency % |
|---|---|---|---|---|---|
| Average | 29 to 34 | 231.0 | 2.5 | 2.17 | 87.5 |
| St. dev. |  | 0.1 | 0.2 | 0.04 | 0.3 |
| Average | 38 to 43 | 231.0 | 2.8 | 2.21 | 87.4 |
| St. dev. |  | 0.1 | 0.2 | 0.04 | 0.2 |
| Average | 51 to 53 | 233.5 | 2.8 | 2.18 | 87.3 |
| St. dev. |  | 0.1 | 0.2 | 0.03 | 0.3 |

In the first period of operation (days 29-34), the effluent concentration of ethylene oxide drops to 2.17 mole percent, slightly below the target of 2.2 mole percent. From day 35 to day 37, an activity decline is observed. As a result, in the second period of operation the overall chloriding effectiveness is increased by increasing the concentration of ethyl chloride in the feed from 2.5 ppmv to 2.8 ppmv while the reaction temperature is held constant at 231° C. The change increases the ethylene oxide concentration in the effluent to about 2.21 mole percent and yields a small reduction in efficiency (about 0.1%). An activity decline is observed between days 44 and 50. Thus, in the third period of operation, the reaction temperature is increased to about 233.5° C. while the concentration of ethyl chloride is held constant at 2.8 ppmv. Again, the catalyst productivity is maintained at an essentially constant value with little loss in efficiency. In commercial plants, a two (2) percent relative variation in the ethylene oxide production rate is considered acceptable.

Comparative Example

This example demonstrates the effect of aging on the optimum overall chloriding effectiveness value, $Z^*$. An autoclave reactor is charged with 70 ml of a high efficiency, rhenium-promoted silver catalyst comprising 34.17% Ag, 469 ppm Cs, 301 ppm Re, 103 ppm SO4, and 117 ppm Mn. The initial reactor feed composition is 30 mole percent $C_2H_4$, 8 mole percent $O_2$, 3 mole percent $CO_2$, 0.9 mole percent $C_2H_6$ and the initial overall chloriding effectiveness value $Z^*$ is 4. The reaction temperature is 275 psig (1997 kPa), and the reaction temperature is 240° C. The gas hourly space velocity is 6400 $h^{-1}$. After a break-in period of three days, ethyl chloride concentration is adjusted to evaluate the effect of $Z^*$.

FIG. 6A depicts efficiency (upper graph, left scale) and $Z^*$ data (lower graph, right scale) as a function of catalyst age. FIG. 6B depicts effluent ethylene oxide concentration (upper graph, left scale) and $Z^*$ data (lower graph, right scale) for the process. At day 9, the overall chloriding effectiveness value, $Z^*$, is changed (at constant temperature) from about 3.5 to about 2.5, resulting in an increase of efficiency of about 2%. The fact that efficiency increases with a decrease in $Z^*$ indicates that a $Z^*$ of 3.5 is above its efficiency-maximizing value early in the catalyst run. However, as the run continues, the catalyst continues to age. At day 24, $Z^*$ is increased back to its initial value of about 3.5. However, the efficiency remains substantially constant, indicating that $Z^*=3.5$ is an efficiency-maximizing value later in the catalyst run. Thus, optimum overall chloriding effectiveness is catalyst age dependent, and the methods described herein account for this age dependence and maintain the catalyst nearer to its true operating optimum.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A process for manufacturing an alkylene oxide by reacting a feed gas comprising an alkylene, oxygen, and an at least one organic chloride over a high efficiency silver catalyst to yield a reaction product comprising the alkylene oxide, wherein the feed gas has an overall catalyst chloriding effectiveness, and the reaction is carried out at a reaction temperature, the process comprising:
   selecting a decrease in at least one of the concentration of the alkylene oxide in the reaction product and the yield of the alkylene oxide;
   varying the overall catalyst chloriding effectiveness and the reaction temperature in an alternating sequence such that when one of the overall catalyst chloriding effectiveness and the reaction temperature is varied, the other of the overall catalyst chloriding effectiveness and the reaction temperature is maintained at a substantially constant value for a selected period of time, wherein the step of varying the overall catalyst chloriding effectiveness and the reaction temperature in an alternating sequence comprises varying one of the overall catalyst chloriding effectiveness and the reaction temperature in response to the selected decrease in at least one of the concentration of the alkylene oxide in the reaction product and the yield of the alkylene oxide.

2. The process for manufacturing an alkylene oxide of claim 1, wherein the step of varying the overall catalyst chloriding effectiveness and the reaction temperature in an alternating sequence comprises maintaining the overall catalyst chloriding effectiveness at a substantially constant first overall catalyst chloriding effectiveness value for a first selected period of time, maintaining the reaction temperature at a substantially constant first reaction temperature value for a second selected period of time, and increasing the overall catalyst chloriding effectiveness from the substantially constant first overall catalyst chloriding effectiveness value to a substantially constant second overall catalyst chloriding effectiveness value at the expiration of the first selected period of time, wherein the first period of time is different from the second period of time.

3. The process for manufacturing an alkylene oxide of claim 1, wherein the step of varying the overall catalyst chloriding effectiveness and the reaction temperature in an alternating sequence comprises maintaining the reaction temperature at a substantially constant first reaction temperature value for a first selected period of time, maintaining the overall catalyst chloriding effectiveness at a substantially constant first overall catalyst chloriding effectiveness value for a second selected period of time, and increasing the reaction temperature from the substantially constant first reaction temperature value to a substantially constant second reaction temperature value at the expiration of the first selected period of time, wherein the first period of time is different from the second period of time.

4. The process of manufacturing an alkylene oxide of claim 1, wherein the selected decrease in the concentration of the alkylene oxide in the reaction product is less than about 0.5 mole percent.

5. The process for manufacturing an alkylene oxide of claim 1, wherein the step of varying the overall catalyst chloriding effectiveness and the reaction temperature in an alternating sequence comprises varying an alternating one of the overall catalyst chloriding effectiveness and the reaction temperature at intervals that correspond to catalyst age increments of less than about 1.0 kt alkylene oxide/m³ catalyst.

6. The process for manufacturing an alkylene oxide of claim 1, wherein the overall catalyst chloriding effectiveness value is represented by the formula:

$$Z^* = \frac{\text{ethyl chloride equivalent }(ppmv)}{\text{ethane equivalent (mole percent)}}$$

wherein the ethyl chloride equivalent is the total concentration in ppmv of ethyl chloride which provides substantially the same catalyst chloriding effectiveness of the at least one organic chloride in the feed gas at the concentration of the at least one organic chloride in the feed gas; and the ethane equivalent is the total concentration in mole percent of ethane which provides substantially the same dechloriding effectiveness as the non-chloride containing hydrocarbons in the feed gas at the concentration of the non-chloride containing hydrocarbons in the feed gas.

7. The process for manufacturing an alkylene oxide of claim 6, wherein the at least one organic chloride is selected from the group consisting of ethyl chloride, ethylene dichloride, and vinyl chloride, and the ethyl chloride equivalent has the following formula:

ethyl chloride equivalent(ppmv)=ECL+2EDC+VCL wherein, ECL is the concentration of ethyl chloride in the feed gas in ppmv, EDC is the concentration of ethylene dichloride in the feed gas in ppmv, and VCL is the concentration of vinyl chloride in the feed gas in ppmv.

8. The process for manufacturing an alkylene oxide of claim 6, wherein the non-chloride containing hydrocarbons in the feed gas comprise at least one selected from the group consisting of ethylene and ethane, and the ethane equivalent has the following formula:

ethane equivalent(mole percent)=$C_2H_6$+0.01$C_2H_4$ wherein, $C_2H_6$ is the concentration of ethane in the feed gas in mole percent, and $C_2H_4$ is the concentration of ethylene in the feed gas in mole percent.

9. The process for manufacturing an alkylene oxide of claim 6, wherein the step of varying the overall catalyst chloriding effectiveness and the reaction temperature in an alternating sequence comprises making alternating increases in the overall catalyst chloriding effectiveness and the reaction temperature, wherein the increases in the catalyst chloriding effectiveness are made in $Z^*$ increments of less than about 5.0 and the increases in reaction temperature are made in increments of less than about 10° C.

10. The process for manufacturing an alkylene oxide of claim 6, wherein $Z^*$ is less than about 20.

11. The process for manufacturing an alkylene oxide of claim 1, wherein the alkylene oxide is ethylene oxide and the alkylene is ethylene.

12. The process for manufacturing an alkylene oxide of claim 1, wherein the organic chloride is at least one selected from ethylene dichloride, ethyl chloride, and vinyl chloride.

13. The process for manufacturing an alkylene oxide of claim 1, wherein the high efficiency silver catalyst includes a rhenium promoter.

14. The process for manufacturing an alkylene oxide of claim 1, wherein the catalyst age is less than about 10 kt alkylene oxide/m³ of catalyst.

15. The process for manufacturing an alkylene oxide of claim 1, wherein the step of varying the overall catalyst chloriding effectiveness and the reaction temperature in an alternating sequence comprises varying the concentration of the at least one organic chloride in the feed gas and the reaction temperature in an alternating sequence.

16. The process for manufacturing an alkylene oxide of claim 1, wherein the step of varying the overall catalyst chloriding effectiveness and the reaction temperature in an alternating sequence comprises varying the overall catalyst chloriding effectiveness and one selected from the flow rate of a reactor coolant fluid and the pressure of a reactor steam coolant in an alternating sequence.

17. The process for manufacturing an alkylene oxide of claim 1, wherein the feed gas further comprises at least one nitrogen-containing promoter.

18. The process for manufacturing an alkylene oxide of claim 17, wherein the feed gas has an overall effectiveness of at least one nitrogen-containing promoter, and when the overall chloriding effectiveness in the feed gas is varied, the overall effectiveness of the at least one nitrogen-containing promoter is varied.

19. The process for manufacturing an alkylene oxide of claim 18, wherein the overall effectiveness of the at least one nitrogen-containing promoter is represented by the formula:

$N^*$=nitric oxide equivalent(ppmv)*($P_{inlet}$/2,300 kPa)

wherein $P_{inlet}$ is the reactor inlet pressure in kilo Pascals and the nitric oxide equivalent is the nitric oxide concentration in ppmv which provides substantially the same promoting effectiveness as the at least one nitrogen-containing promoter.

20. The process of manufacturing an alkylene oxide of claim 19, further comprising selecting a ratio of the overall effectiveness of the at least one nitrogen-containing promoter to the overall chloriding effectiveness, wherein when the overall chloriding effectiveness is varied, the overall effectiveness of the at least one nitrogen-containing promoter is varied to maintain the selected ratio.

* * * * *